United States Patent
Taniguchi et al.

(10) Patent No.: US 10,408,901 B2
(45) Date of Patent: Sep. 10, 2019

(54) MAGNETIC RESONANCE IMAGING DEVICE AND METHOD FOR ADJUSTING WAVEFORM OF GRADIENT MAGNETIC FIELD AND MEASURING ECHO SIGNALS BY APPLYING THE ADJUSTED WAVEFORM TO A PULSE SEQUENCE

(71) Applicant: Hitachi, Ltd., Tokyo (JP)

(72) Inventors: Yo Taniguchi, Tokyo (JP); Toru Shirai, Tokyo (JP); Hisaaki Ochi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 264 days.

(21) Appl. No.: 15/313,983

(22) PCT Filed: May 19, 2015

(86) PCT No.: PCT/JP2015/064361
§ 371 (c)(1),
(2) Date: Nov. 25, 2016

(87) PCT Pub. No.: WO2015/190244
PCT Pub. Date: Dec. 17, 2015

(65) Prior Publication Data
US 2017/0192068 A1   Jul. 6, 2017

(30) Foreign Application Priority Data

Jun. 9, 2014 (JP) ................. 2014-118669

(51) Int. Cl.
*G01R 33/385* (2006.01)
*A61B 5/055* (2006.01)
(Continued)

(52) U.S. Cl.
CPC .......... *G01R 33/3854* (2013.01); *A61B 5/055* (2013.01); *G01R 33/288* (2013.01); *G01R 33/561* (2013.01)

(58) Field of Classification Search
USPC .................................. 324/300–322
See application file for complete search history.

(56) References Cited

U.S. PATENT DOCUMENTS

| 4,680,545 A | 7/1987 | Gray et al. |
| 5,276,397 A * | 1/1994 | Kawasaki ........ G01R 33/56509 |
| | | 324/300 |
| 2009/0160440 A1 | 6/2009 | Yui |

FOREIGN PATENT DOCUMENTS

| JP | 01-214352 A | 8/1989 |
| JP | 01-249042 A | 10/1989 |

(Continued)

OTHER PUBLICATIONS

International Preliminary Report on Patentability received in corresponding International Application No. PCT/JP2015/064361 dated Dec. 22, 2016.
(Continued)

*Primary Examiner* — Jay Patidar
(74) *Attorney, Agent, or Firm* — Mattingly & Malur, PC

(57) ABSTRACT

Acoustic noise reduction is achieved in a high-speed imaging method such as a phase-compensation type GE sequence, which is not provided with sufficiently long intervals for applying the gradient magnetic field pulses. A band-stop filter is used to reduce components of a frequency band in the gradient magnetic field waveform, having a high sound pressure level being a source of sound, thereby performing the noise reduction. In general, when a band of the gradient magnetic field is reduced, the waveform is likely to be considerably distorted, failing to satisfy imaging conditions. Therefore, the distorted waveform is shaped so that the imaging conditions are satisfied. The sound pressure level of the gradient magnetic field waveform is calculated by using a response function inherent to the device.

18 Claims, 20 Drawing Sheets

(51) Int. Cl.
*G01R 33/561* (2006.01)
*G01R 33/28* (2006.01)

(56) References Cited

FOREIGN PATENT DOCUMENTS

JP 04-208134 A 7/1992
JP 2009-165817 A 7/2009

OTHER PUBLICATIONS

Robert A. Hedeen, et al., "Characterization and Prediction of Gradient Acoustic Noise in MR Imagers", MRM 37:7-10 (1997), pp. 7-10.
F. Hennel, et al., "Silent" MRI With Soft Gradient Pulses, Magnetic Resonance in Medicine 42:6-10 (1999), pp. 6-10.
International Search Report of PCT/JP2015/064361 dated Aug. 18, 2015.

* cited by examiner (a)

(b)

(a)

(b)

(c)

(a)

| | | s | p | f | [dB] 810 |
|---|---|---|---|---|---|
| | Gx | 110 | 108 | 107 | |
| | Gy | 112 | 107 | 112 | |
| | Gz | 114 | 107 | 112 | |

(b)

| | | s | p | f | 820 |
|---|---|---|---|---|---|
| | Gx | 103 | 101 | 101 | |
| | Gy | 108 | 101 | 108 | |
| | Gz | 111 | 100 | 108 | |

(c)

| | | s | p | f | 830 |
|---|---|---|---|---|---|
| | Gx | -7 | -7 | -6 | |
| | Gy | -4 | -7 | -4 | |
| | Gz | -3 | -7 | -3 | |

(d)

| | | s | p | f | 840 |
|---|---|---|---|---|---|
| | Gx | -9 | -7 | -14 | |
| | Gy | -4 | -7 | -8 | |
| | Gz | -3 | -7 | -16 | |

(e)

| | | s | p | f | 850 |
|---|---|---|---|---|---|
| | Gx | -6 | -7 | -7 | |
| | Gy | -2 | -6 | -3 | |
| | Gz | -3 | -6 | -3 | |

FIG.18

MAGNETIC RESONANCE IMAGING DEVICE AND METHOD FOR ADJUSTING WAVEFORM OF GRADIENT MAGNETIC FIELD AND MEASURING ECHO SIGNALS BY APPLYING THE ADJUSTED WAVEFORM TO A PULSE SEQUENCE

TECHNICAL FIELD

The present invention relates to a technique of magnetic resonance imaging (MRI). More particularly, the present invention relates to a technique for reducing acoustic noise caused by a gradient magnetic field.

BACKGROUND ART

A magnetic resonance imaging (MRI) device is a medical-use image capturing system that generates nuclear magnetic resonance in hydrogen nuclei within any plane traversing a test subject, and takes a tomographic image within the plane, based on nuclear magnetic resonance signals being generated. In general, a slice gradient magnetic field is applied for identifying an imaging plane, simultaneously with providing exciting pluses that excite magnetization within the plane. Accordingly, nuclear magnetic resonance signals (echoes) are obtained, which are generated at a stage of convergence of magnetization that has been excited. In addition, a phase encoding gradient magnetic field and a frequency encoding gradient magnetic field, being orthogonal to each other within the tomographic plane, are applied for providing the magnetization with positional information, during a period from the excitation until obtaining the echoes.

The pulses and each of the gradient magnetic fields for generating echoes are applied according to a predetermined pulse sequence. Various pulse sequences are known depending on purposes. For example, there is a gradient echo (GE) type high-speed imaging method that applies gradient magnetic fields while applying exciting pulses repeatedly at relatively short intervals, and acquires echoes.

In this high-speed imaging method, a trapezoid wave of the gradient magnetic field, having nearly maximum amplitude, is turned on and off at high speed, and therefore, extremely loud noise, 100 dB or more, is generated within a bore where the test subject is placed. This noise has loudness considerably jarring the test subject placed in the bore, even though the test subject wears headphones or earplugs. Since this type of noise becomes louder, as a level of magnetization becomes higher, countermeasures are needed against a high magnetic-field machine of 3 T (tesla) or higher.

As one of the countermeasures, there is a method of acoustic noise reduction by allowing the trapezoidal wave of the gradient magnetic field to pass through a low-pass filter, and smoothing variation of amplitude at a rise time and a fall time of the wave (e.g., see Non Patent Document 1). In addition, sound generated by the gradient magnetic field is expressed by a product of a frequency distribution of the gradient magnetic field waveform and a frequency response function (FRF) inherent to the device. By utilizing this feature, there is a method of using a low-pass filter to reduce a frequency component of the gradient magnetic field in a range where the FRF exceeds a minimal level, thereby canceling the noise (e.g., see Non Patent Document 2).

PRIOR ART DOCUMENT

Non Patent Document

Non Patent Document 1
Hedeen R A, Edelstein W A. "Characterization and Prediction of Gradient Acoustic Noise in MR Imagers" Magn Reson Med 1997; 37: p. 7-10
Non Patent Document 2
Hennel F, Girard F, Loenneker T. ""Silent" MRI With Soft Gradient Pulses", Magn Reson Med 1999; 42: p. 6-10

DISCLOSURE OF THE INVENTION

Problems to be Solved by the Invention

For example, when the method described in the aforementioned Patent Document 2 is applied to the FSE (fast spin echo) sequence that is frequently used for imaging a head portion, it is reported that a sound pressure level is decreased by 6 to 17 dB. It should be noted that in MRI, a time integral value of the gradient magnetic field or amplitude thereof within a partial zone determines imaging conditions, such as spatial resolution and a field of view. Therefore, it is necessary to maintain the time integral value and the amplitude without change, even after the noise reduction, and thus, this may cause elongation of time for applying the gradient magnetic field after the noise reduction according to this method.

Accordingly, this method cannot be applied to a pulse sequence that does not have a sufficiently long interval between the gradient magnetic field pulses.

For example, in the GE type high-speed imaging method as described above, in many cases, the application time of the pulses of the gradient magnetic field is made shorter as possible, in order to reduce imaging time and to enhance a quality of image. Therefore, it is not allowed to elongate the application time of the pulses for the purpose of noise reduction, and thus it is difficult to apply the aforementioned method. In particular, in a pulse sequence as one of the GE type sequences, where a gradient magnetic field pulse is added for resetting the time integral of the gradient magnetic fields on respective axes (phase-compensation type GE sequence), there is little time period when the gradient magnetic field is not applied, and thus noise reduction by varying waveforms is basically difficult.

The present invention has been made in view of the circumstances as described above, and an object of the present invention is to provide a technique to reduce acoustic noise in a high-speed imaging method that does not have sufficiently long intervals for applying the gradient magnetic field pulses.

Means for Solving the Problems

The present invention is directed to acoustic noise reduction by using a band-stop filter to reduce a component of a gradient magnetic field waveform, in a high frequency band with a high sound pressure level, which is a source of noise generation. In general, when a frequency band of the gradient magnetic field waveform is reduced, the waveform is likely to be distorted considerably, failing to satisfy the imaging conditions. Accordingly, this distorted waveform is subjected to shaping so as to satisfy the imaging conditions. The sound pressure level of the gradient magnetic field waveform is calculated by using a response function inherent to the device.

Specifically, there is provided a magnetic resonance imaging device including a gradient magnetic field waveform adjuster for adjusting an initial waveform being a gradient magnetic field waveform preset in a pulse sequence, so as to obtain an adjusted waveform, wherein, the pulse sequence is used for irradiating a test subject placed in a static magnetic field, with a high-frequency magnetic field according to a predetermined imaging condition, applying the gradient magnetic field, and measuring an echo signal generated from the test subject, and the gradient magnetic field waveform adjuster is provided with, a band-rejection section configured to filter out a part of a frequency band of the initial waveform to generate a filtered waveform, and a waveform shaper configured to perform shaping of the filtered waveform so as to satisfy the imaging condition, and to obtain the adjusted waveform.

In addition, there is provided a method of adjusting a gradient magnetic field waveform by a magnetic resonance imaging device, including the steps of, filtering out a part of a frequency band of an initial waveform being the waveform of the gradient magnetic field, so as to generate a filtered waveform, and performing shaping of the filtered waveform in such a manner that predetermined imaging condition is satisfied.

Advantage of the Invention

According to the present invention, is possible to reduce noise, even in the high-speed imaging method that is not provided with a sufficiently long interval between the gradient magnetic field pulses.

BRIEF DESCRIPTION OF THE DRAWINGS

FIG. 18(a) shows summations of the sound pressure levels in each of the axial directions of the initial waveforms, FIG. 18(b) shows summations of the sound pressure levels in each of the axial directions of the adjusted waveforms, FIG. 18(c) shows differences between FIGS. 18(a) and 18(b) as an embodiment of the present invention, FIG. 18(d) shows differences between FIG. 18(a) and the summations of the sound pressure levels in each of the axial directions of the adjusted waveforms after shaping the waveforms, as a modification example 1 of the present invention, and FIG. 18(e) shows differences between the FIG. 18(a) and the summations of the sound pressure levels in each of the axial directions of the adjusted waveforms when the band-stop filter is used according to a modification example 2 of the present invention;

BEST MODE FOR CARRYING OUT THE INVENTION

Figure 1:
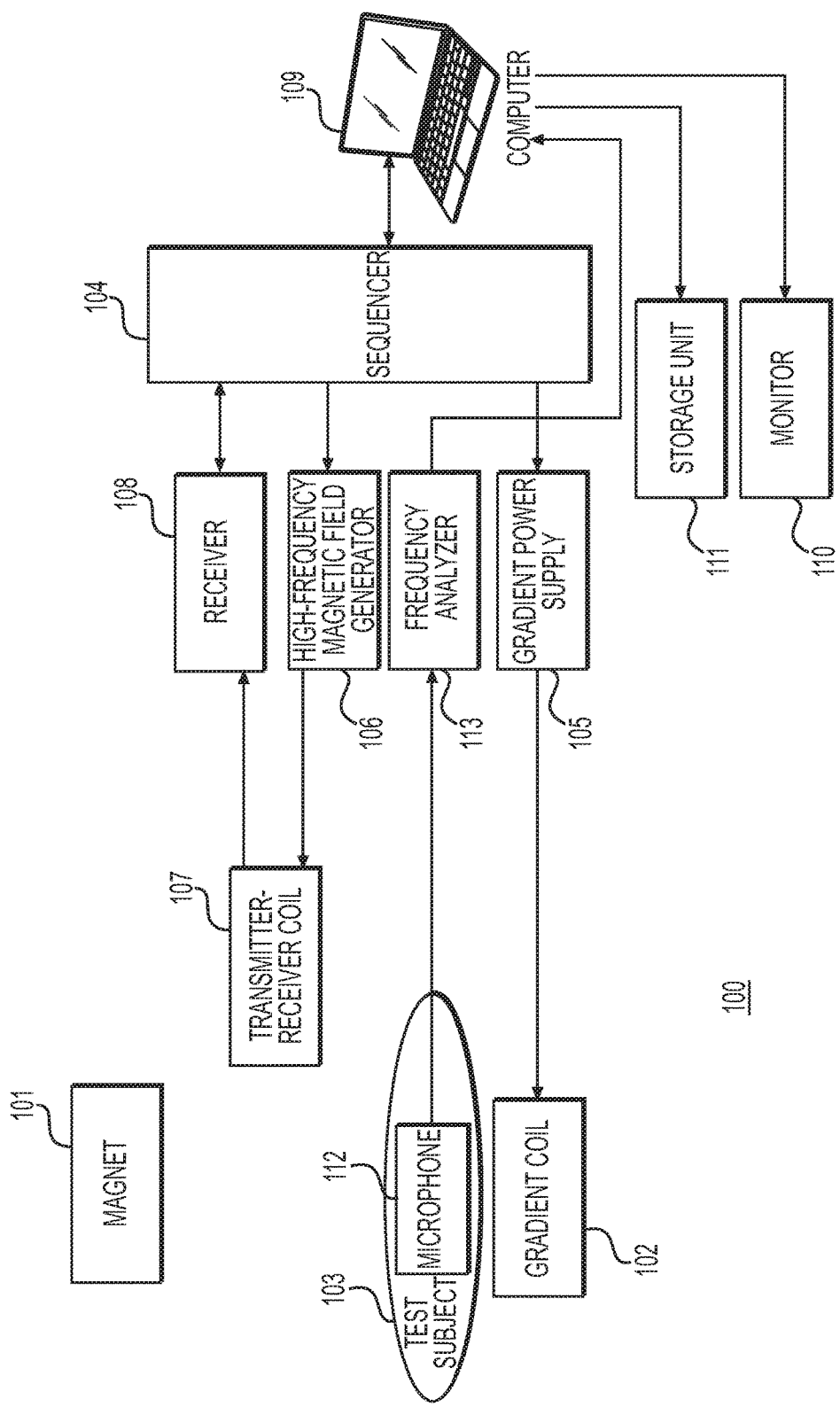
FIG. 1 is a block diagram showing a schematic configuration of an MRI device as an embodiment of the present invention.

An embodiment to which the present invention is applied will now be described. Hereinafter, in all the figures illustrating the embodiment of the present invention, elements with an identical function are labeled with the same reference numeral, unless otherwise specified, and they will not be redundantly explained.

[MRI Device Configuration]

Firstly, an MRI device of the present embodiment will be described. FIG. 1 is a block diagram showing a schematic configuration of the MRI device 100 of the present embodiment. The MRI device 100 is provided with a magnet 101 for generating a static magnetic field, a gradient coil 102 for generating a gradient magnetic field, a sequencer 104, a gradient power supply 105, a high-frequency magnetic field generator 106, a transmitter-receiver coil 107 for irradiation of a high-frequency magnetic field and detection of a nuclear magnetic resonance signal, a receiver 108, a computer 109, a monitor 110, and a storage unit 111. The transmitter-receiver coil 107 is shown as a single unit in the figure, but a transmitter coil and a receiver coil may be provided separately.

The gradient coil 102 is provided with coils Gx, Gy, and Gz for applying the gradient magnetic fields, respectively to the directions of x, y, and z of a device coordinate system of the MRI device 100. In response to an instruction from the gradient power supply 105, the gradient magnetic fields are applied from those coils, respectively.

The MRI device 100 of the present embodiment is further provided with a microphone 112 and a frequency analyzer 113 which are used for calculating a response function inherent to the MRI device 100 of the present embodiment. The microphone 112 is disposed in proximity to a test subject, collects sound that is generated when the gradient magnetic fields are applied, and then converts the sound into electric signals. The frequency analyzer 113 obtains a spectrum from the sound collected via the microphone 112.

The test subject (e.g., living body) 103 is placed on a bed (table) within static magnetic space generated by the magnet 101. The sequencer 104 sends instructions to the gradient power supply 105 and to the high-frequency magnetic field generator 106, and the gradient magnetic field and the high-frequency magnetic field are generated therefrom, respectively. The high-frequency magnetic field is applied to the test subject 103, via the transmitter-receiver coil 107. A nuclear magnetic resonance signal generated from the test subject 103 is received by the transmitter-receiver coil 107, and the signal is detected by the receiver 108. The sequencer 104 sets a nuclear magnetic resonance frequency (detection reference frequency f0) which is a reference of detection. The detected signal is transmitted to the computer 109, and subjected to signal processing such as an image reconstruction therein. A result of the signal processing is displayed on the monitor 110. If required, it is possible to store the detected signals and measuring conditions in the storage unit 111.

The sequencer 104 performs control so as to operate each unit at a timing and intensity being programmed in advance, according to instructions from the computer 109. A sequence, which describes in particular, the timing and intensity of the high-frequency magnetic field, the gradient magnetic fields, and signal receiving, is referred to as a pulse sequence (imaging sequence). In the MRI device 100 of the present embodiment, any pulse sequence is available.

The microphone 112 is connected to the computer 109, via the frequency analyzer 113. The microphone 112 collects sound that is generated when the gradient magnetic fields are applied and converts the sound into electric signals, and thereafter, the frequency analyzer 113 converts the signals into a spectrum, and inputs the spectrum in the computer 109. The computer 109 calculates the response function, according to the waveforms of thus applied gradient magnetic fields and the spectrum inputted from the frequency analyzer 113.

[Functional Block of the Computer]

The computer 109 of the present embodiment controls each part of the MRI device 100 and executes imaging. In the present embodiment, gradient magnetic field waveforms are adjusted so as to reduce noise that is caused by applying the gradient magnetic fields.

Figure 2:
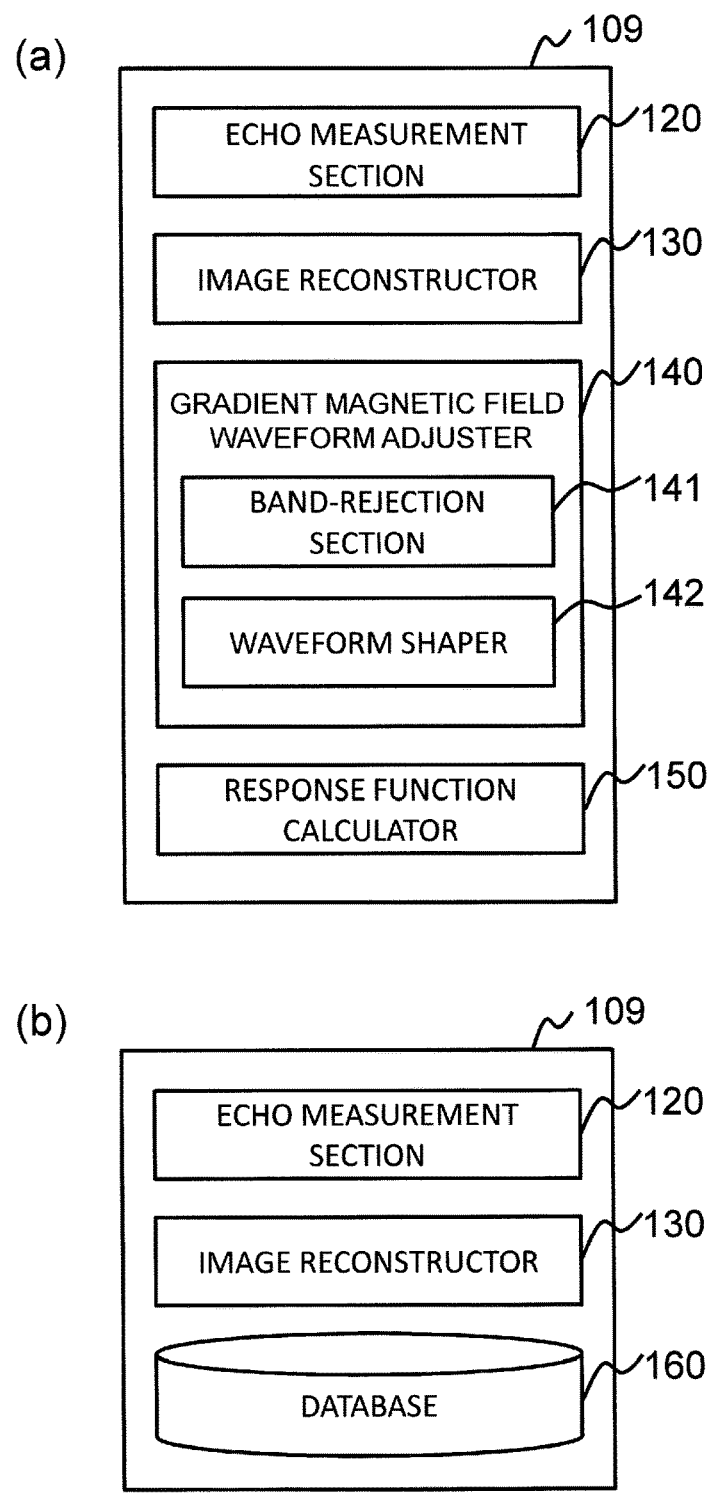
FIG. 2(a) is a functional block diagram of a computer as an embodiment of the present invention.
FIG. 2(b) is a functional block diagram of the computer as a modification example of the embodiment of the present invention.

In order to achieve this function, as shown in FIG. 2, the computer 109 of the present embodiment is provided with, an echo measurement section 120 that irradiates the test subject 103 placed in a static magnetic field with the high-frequency magnetic field, simultaneously with applying the gradient magnetic field thereto according to a predetermined imaging condition and a pulse sequence, measures echo signals generated from the test subject 103, and places the signals in k-space, an image reconstructor 130 that reconstructs an image from the echo signals, a gradient magnetic field waveform adjuster 140 that adjusts an initial waveform being the gradient magnetic field waveform set in the pulse sequence, and obtains an adjusted waveform, and a response function calculator 150 that acquires the response function. This echo measurement section 120 applies the adjusted waveform to the pulse sequence, instead of the initial waveform, thereby measuring the echo signals.

A CPU of the computer 109 loads programs stored in the storage unit 111 and executes them, thereby implementing each of those functions above. It should be noted that all the functions above are not necessarily implemented by software, but apart or all of them may be implemented by hardware such as ASIC (Application Specific Integrated Circuit) and FPGA (field-programmable gate array) circuit.

[Pulse Sequence]

In the present embodiment, the pulse sequence followed by the echo measurement section 120 will be described, taking a GE based pulse sequence of phase compensation type (phase-compensation type GE sequence) as an example. Firstly, this phase-compensation type GE sequence will be described.

Figure 3:
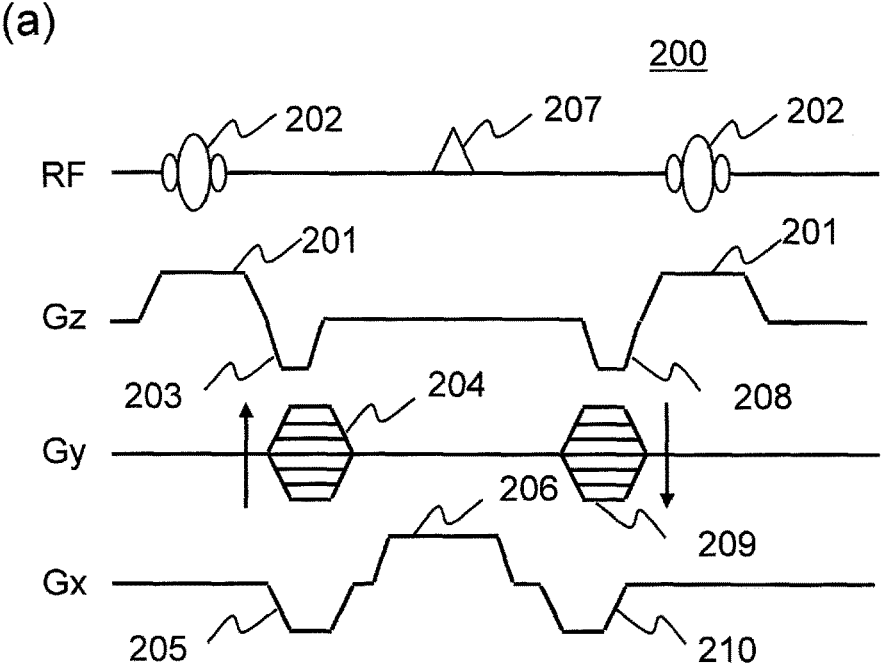
FIG. 3(a) is a sequence diagram showing a phase-compensation type GE sequence as an embodiment of the present invention.
FIG. 3(b) illustrates a K-space configuration.
Figure 3:
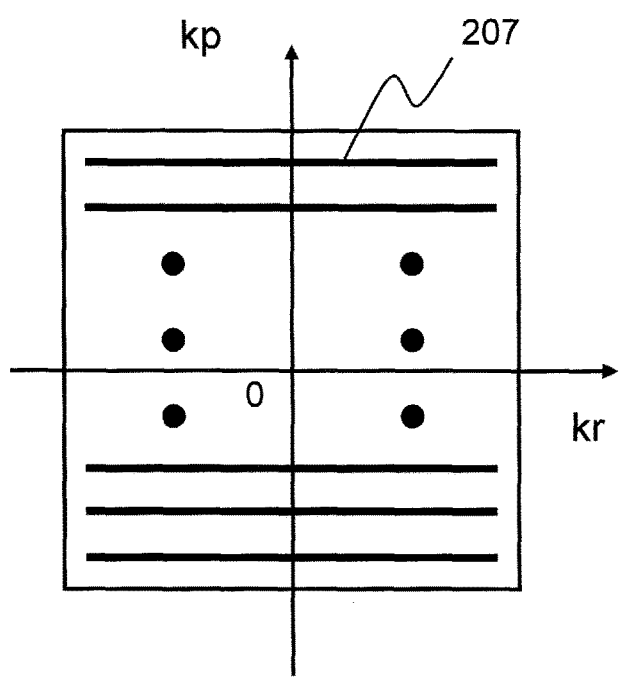

FIG. 3 illustrates a sequence diagram of the phase-compensation type GE sequence 200. In this figure, RF, Gs, Gp, and Gr represent respectively, a high-frequency magnetic field, a slice gradient magnetic field, a phase encoding gradient magnetic field, and a frequency encoding gradient magnetic field.

In the phase-compensation type GE sequence 200, a gradient magnetic field pulse for obtaining zero as a time product value of the gradient magnetic fields of respective axes, is added to a normal GE sequence. A flip angle is generally larger relative to the angle when GrE method is used, and the phases are inverted alternately. As for a repetition time TR, it is relatively short and around 5 ms.

According to the phase-compensation type GE sequence 200, firstly, irradiation of the high-frequency magnetic field (RF) pulses 202 is performed, along with applying the slice gradient magnetic field 201, thereby exciting magnetization of slices within the subject body. Next, a slice rephasing gradient magnetic field 203, a phase encoding gradient magnetic field 204 for adding positional information in the phase encoding direction to the phase of magnetization, and a frequency encoding gradient magnetic field for dephasing 205 are applied, and thereafter, a magnetic resonance signal (echo) 207 is measured along with applying a frequency encoding gradient magnetic field 206 for adding positional information in the readout direction. And finally, the gradient magnetic fields 208, 209, and 210 are applied so that the time integral value of the gradient magnetic fields of the respective axes becomes zero. In the following description, the echo measuring period is referred to as "A/D period".

The procedure described above is repeated every repetition time TR, while varying the amplitude of the phase encoding gradient magnetic fields 204 and 209 (phase encoding amount kp), along with changing the phase of the RF pulse by 180 degrees, and then echoes are measured, which are required for obtaining one piece of image. As shown in FIG. 3(b), the echoes 207 are placed in the k-space, and an image is reconstructed according to an inverse Fourier transform.

When the phase-compensation type GE sequence 200 is used, an image that emphasizes T1 (longitudinal relaxation time) can be obtained. The obtained image shows contrast reflecting T2 (transverse relaxation time)/T1, having high contrast between tissue and blood, and accordingly, it is widely used for cardiac morphological/functional diagnosis and abdominal shape diagnostics.

In the present embodiment, a group of the gradient magnetic fields, among the constitutional elements of the aforementioned sequence, are adjusted so as to achieve noise reduction. The group of gradient magnetic fields may include three types, in association with functions, respectively; the slice gradient magnetic field 201, the phase encoding gradient magnetic field 204, and the frequency encoding gradient magnetic field 206. In the following description, the group of gradient magnetic fields, applied in the axial directions of the slice gradient magnetic field 201 (in the phase-compensation type GE sequence 200 described above, the slice gradient magnetic field 201, the slice rephasing gradient magnetic field 203, and the gradient magnetic field 208) are collectively referred to as the slice gradient magnetic field s. Similarly, a group of gradient magnetic fields applied in the axial direction of the phase encoding gradient magnetic field 204 are collectively referred to as the phase encoding gradient magnetic field p, and the group of gradient magnetic fields applied in the axial direction of the frequency encoding gradient magnetic field 206 are collectively referred to as the frequency encoding gradient magnetic field f.

[Gradient Magnetic Field Waveforms]

Figure 4:
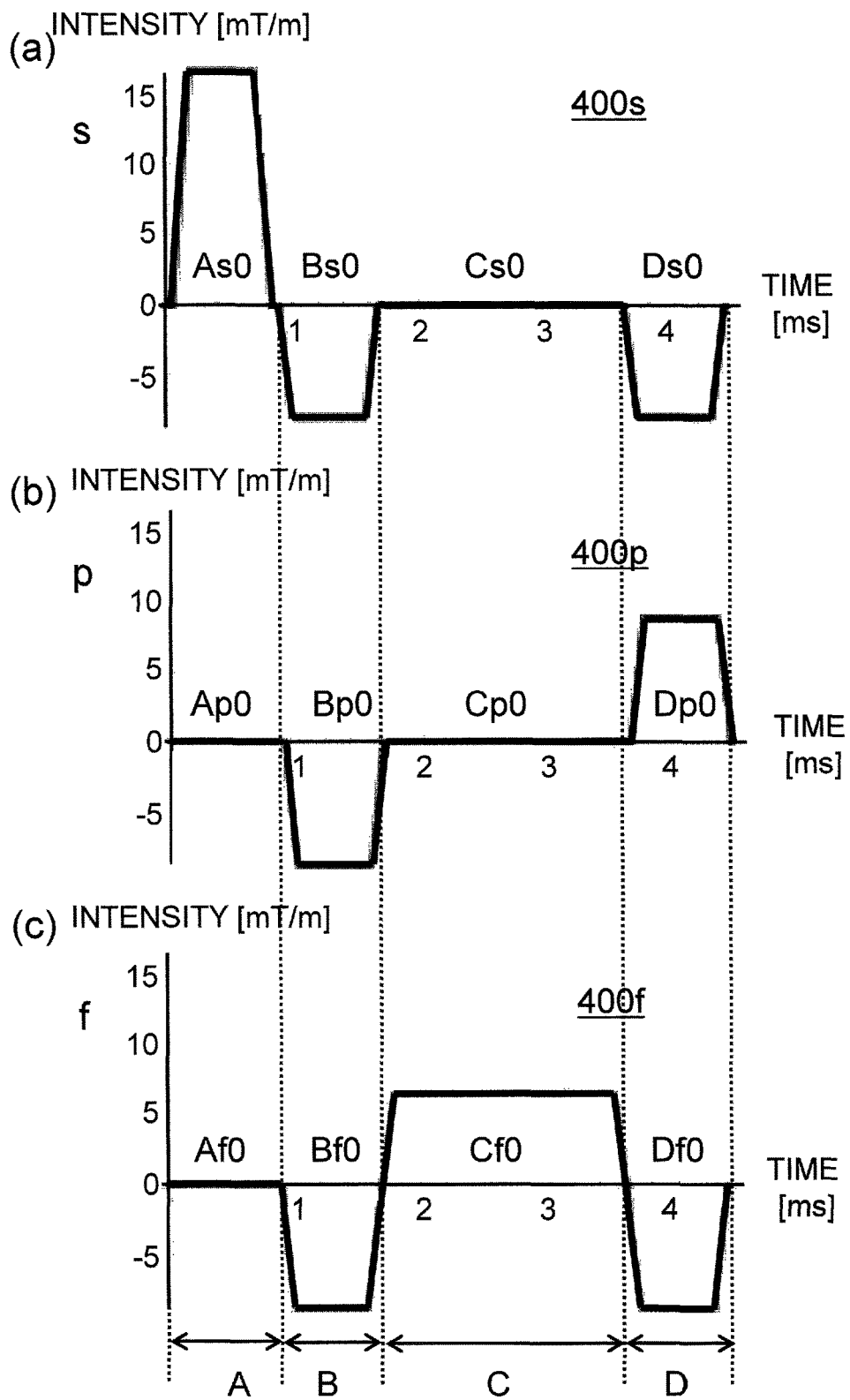
FIGS. 4(a) to 4(c) illustrate gradient magnetic field waveforms of the phase-compensation type GE sequence as an embodiment of the present invention.

FIGS. 4(a) to 4(c) illustrate the gradient magnetic field waveforms 400s, 400p, and 400f respectively of the aforementioned three types gradient magnetic fields (slice gradient magnetic field s, phase encoding gradient magnetic field p, and frequency encoding gradient magnetic field f; also referred to as gradient magnetic fields in the respective axial directions s, p, and f). The gradient magnetic field waveforms as shown in the figures are initial waveforms set in the phase-compensation type GE sequence 200 for the first time.

When echoes are measured, the gradient magnetic fields in the axial directions s, p, and f, are distributed to the gradient coils in the axes of x, y, and z (Gx, Gy, and Gz), respectively, thereby determining the angle of the imaging plane. By way of example, as shown in FIG. 3, when it is configured as (s, p, f)=(z, y, x), an image on the axial plane is taken, and when it is configured as (s, p, f)=(x, y, z), an image on the sagittal plane is taken.

As shown in the figures, each of the gradient magnetic field waveforms (initial waveforms) 400s, 400p, and 400f in the s, p, and f axial directions comprises trapezoid waves, being turned on or off in each of four zones A, B, C, and D. The zone A includes irradiation of RF pulse 202. The zone C includes an echo signal measuring (A/D) period 207. The zone B is positioned between the zones above, and the zone D is a period between the end of the zone C and the start of the zone A for the next repetition time.

The gradient magnetic field (trapezoid wave) applied in each of the zones is referred to as As, Bs, Bp, Bf, Cf, Ds, Dp, and Df, and in particular, the trapezoid waves of each of the initial waveforms are referred to as As0, Bs0, Bp0, Bf0, Cf0, Ds0, Dp0, and Df0, as shown in FIGS. 4(a) to 4(c). It should be noted that the period of actual RF irradiation (referred to as "RF period") in the zone A only corresponds to a period when the intensity of As0 is constant. Similarly, the period of actual measurement of echo signal (A/D) (referred to as "A/D period") in the zone C only corresponds to a period when the intensity of Cf0 is constant.

By way of example, in the phase-compensation type GE sequence 200 as shown in FIG. 3(a), As0 is the slice gradient magnetic field 201, Bs0 is the slice rephasing gradient magnetic field 203, and Ds0 is the gradient magnetic field 208. Bp0 is the phase encoding gradient magnetic field 204, and Dp0 is the gradient magnetic field 209. In addition, Bf0 is the frequency encoding gradient magnetic field for dephasing 205, Cf0 is the frequency encoding gradient magnetic field 206, and Df0 is the gradient magnetic field 210.

[Adjustment of Gradient Magnetic Field Waveforms]

The gradient magnetic field waveform adjuster 140 transforms the gradient magnetic field waveforms (initial waveforms) set in advance in the pulse sequence (phase-compensation type GE sequence 200), and performs adjustment of the gradient magnetic field waveforms, so as to achieve noise reduction.

It is difficult to apply a low-pass filter in the phase-compensation type GE sequence 200 due to time constraints. In the present embodiment, a band-stop filter for reducing a desired frequency band, is used to reduce (filter out) a frequency band where a sound pressure level is high, thereby lowering the sound pressure level and achieving noise reduction. The sound pressure level of the noise generated by the gradient magnetic fields that are applied in the phase-compensation type GE sequence 200 is calculated by using the response function inherent to device (FRF).

At this moment, if only the band-stop filter is applied, waveforms being generated do not satisfy the imaging conditions. Therefore, in the present embodiment, the waveforms after applying the band-stop filter (filtered waveform) are shaped in such a manner that the imaging conditions are satisfied, without extending the application time of the gradient magnetic fields.

For implementing this shaping, as shown in FIG. 2, the gradient magnetic field waveform adjuster 140 of the present embodiment, is provided with a band-rejection section 141 configured to filter out a part of the frequency band of the initial waveform, and a waveform shaper 142 configured to shape the filtered waveform in such a manner that the imaging conditions are satisfied and to obtain an adjusted waveform.

[Band Rejection Section]

The band-rejection section 141 filters a frequency band where a sound pressure level becomes equal to or higher than a predetermined level, out of the frequency band of the initial waveform, and obtains a filtered waveform. The sound pressure level of the initial waveform is calculated by using the response function inherent to the MRI device 100. A band-stop filter configured to reduce a desired frequency band is used to filter out the frequency band.

Unlike a low-pass filter or a high-pass filter, the band-stop filter allows passage of low frequencies and high frequencies of the frequency band that configures the waveform, but filters out only frequencies in a specific middle band. The frequency band to be filtered can be set exclusively.

The sound pressure level of the frequency band to be reduced (filtered) may be determined in advance, on a device basis or on a pulse sequence basis to be used. It is further possible to configure such that the sound pressure level of the frequency band in the initial waveform is calculated firstly, and thereafter, the result is presented for a user to determine the sound pressure level for filtering out.

[Waveform Shaper]

As described above, areas of the trapezoid waves As, Bs, Bp, Bf, Cf, Ds, Dp, and Df, respectively applied to the four zones shown in A, B, C, and D in FIG. 4(a), intensity of As applied during the irradiation of the RF pulse 202, and intensity of Cf applied while receiving signals (during A/D), are determined by the imaging conditions. If those values are changed, a desired image cannot be obtained. Therefore, the waveform shaper 142 shapes the filtered waveform in such a manner that the imaging conditions are satisfied.

The waveform shaper 142 of the present embodiment shapes the filtered waveforms respectively of the RF period and the A/D period, in such a manner that the initial waveform of each period can be reconstituted (restored), so as to obtain adjusted waveforms. Specifically, the trapezoid waves of the initial waveforms (waveforms having constant intensity) are reconstituted as the filtered waveforms respectively in the s, p, and f axial directions during the RF period when the RF pulse 202 is applied. In addition, the trapezoid waves of the initial waveforms (waveforms having constant intensity) are reconstituted as the filtered waveforms respectively in the s, p, and f axial directions during the A/D period.

The waveform shaper 142 of the present embodiment modifies the intensity of the filtered waveform, in such a manner that a summation (time integral value) of the areas (signed) of the areas of the filtered waveform, as to each of the s, p, and f axial directions, becomes equal to a summation (time integral value) of the areas (signed) of the initial waveform, whereby shaping of the filtered waveform is performed. This shaping is performed so as to maintain the application amount of the gradient magnetic fields in the s, p, and f axial directions, respectively. Accordingly, the imaging conditions of the initial waveforms are satisfied. Intensity of the filtered waveforms is changed, without extending the application time of the gradient magnetic fields in all the four zones. That is, the waveform shaping is performed only by adjusting the intensity of the filtered waveforms.

[Response Function Acquisition Section]

A response function calculator 150 applies an already-known gradient magnetic field waveform, and according to a spectrum of sound generated therefrom, a response function of the MRI device 100 is obtained. In other words, the spectrum obtained from the sound that is measured while applying the already-known gradient magnetic field is divided by the spectrum obtained via a Fourier transform of the already-known gradient magnetic field being applied, thereby calculating the response function. As the already-known gradient magnetic field waveform, white noise may be used, for instance. Since the spectrum of the gradient magnetic field in the form of white noise is constant, the spectrum measured by applying this gradient magnetic field as it is, serves as the response function.

As described above, the sound generated by applying the already-known gradient magnetic field waveform is collected by a microphone 112, transformed into electrical signals, further converted into a spectrum by the frequency analyzer 113, and then inputted into the response function calculator 150.

[Flow of the Gradient Magnetic Field Waveform Adjusting Process]

Figure 5:
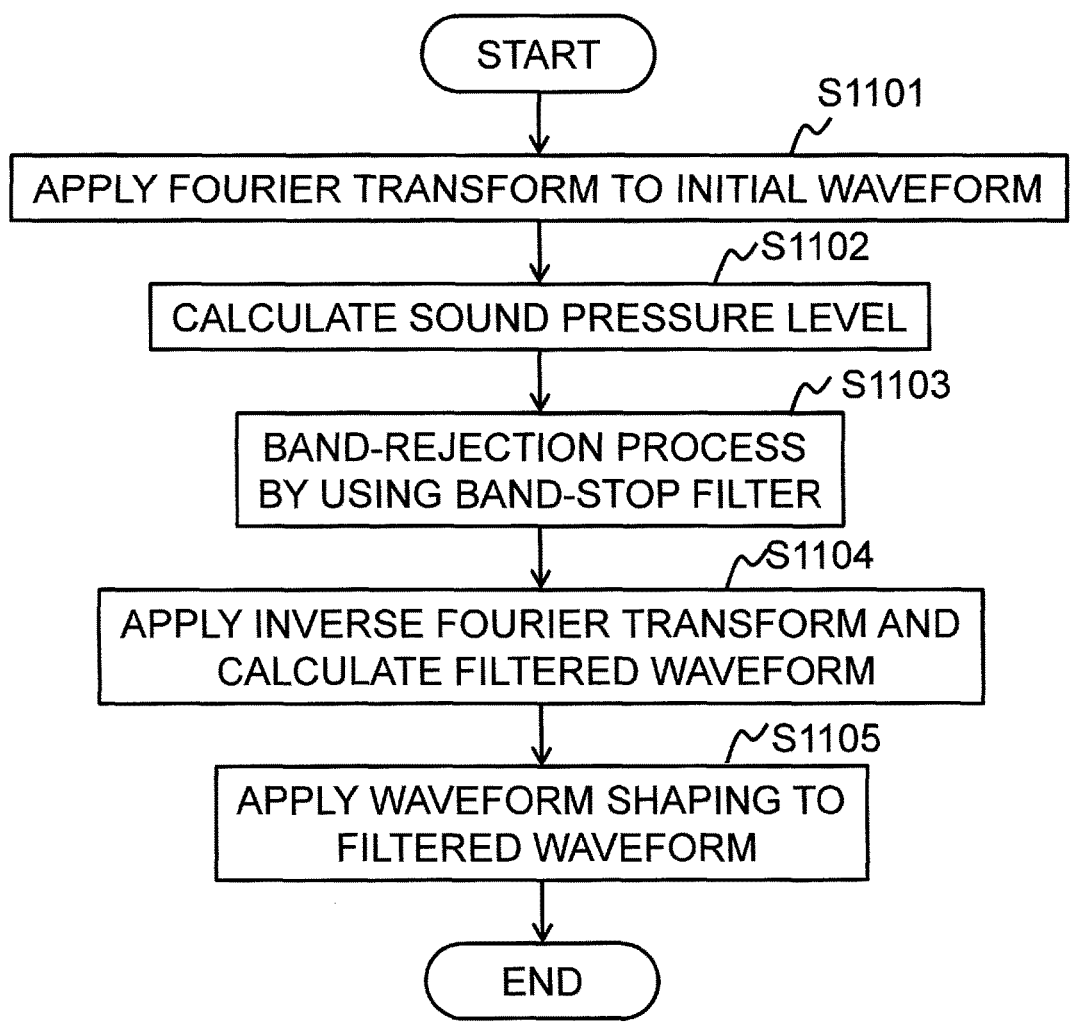
FIG. 5 is a flowchart showing a process for adjusting the gradient magnetic field waveform, as an embodiment of the present invention.

There will be described a processing flow of the gradient magnetic field waveform adjustment according to the gradient magnetic field waveform adjuster 140 of the present embodiment. FIG. 5 is a flowchart of the gradient magnetic field waveform adjusting process of the present embodiment. The response function inherent to the MRI device 100 used for the band filtering process is calculated in advance.

Firstly, the band-rejection section 141 applies the Fourier transform to the gradient magnetic field waveforms (initial waveform) set in advance in the phase-compensation type GE sequence 200, and transforms the gradient magnetic field waveform into a frequency distribution (step S1101). Next, the band-rejection section 141 multiplies the frequency distribution being obtained, by the response function 310 inherent to the MRI device 100, thereby obtaining a sound pressure level (step S1102).

The band-rejection section 141 performs the band-stop filtering process (step S1103). The band-rejection section 141 applies a band-stop filter for reducing a frequency band where the sound pressure level has a value equal to or higher than a predetermined threshold, to the frequency distribution obtained by step S1101, thereby performing the band-rejection process.

The band-rejection section 141 applies a reverse Fourier transform for reconstituting the gradient magnetic field waveform, from the frequency distribution after the band-rejection (step S1104). The gradient magnetic field waveform thus obtained is referred to as a filtered waveform.

The waveform shaper 142 performs a waveform shaping process for shaping the gradient magnetic field waveform, so that the imaging conditions are satisfied (step S1105).

[Gradient Magnetic Field Waveform Adjusting Process]

Next, there will be described each step of the gradient magnetic field waveform adjusting process comprising the aforementioned band-rejection process and the waveform shaping process, along with a specific example.

In actual imaging, a series of pulses as shown in the phase-compensation type GE sequence 200 of FIG. 3 are applied repeatedly. In other words, the gradient magnetic fields respectively in the s, p, and f axial directions as shown in FIGS. 4(a) to 4(c), are repeatedly applied.

In the following, the gradient magnetic field waveform (initial waveform) 410 targeted for waveform adjustment will be described, taking as an example that the initial waveforms 400s, 400p, and 400f as shown in FIGS. 4(a) to 4(c) are applied five times, as illustrated in FIG. 6(a). In FIG. 6(a), the horizontal axis represents time [ms] and the vertical axis represents intensity [mT/m].

[Step S1101]

FIG. 6(b) shows that the band-rejection section 141 performs sampling at 65 kHz of the initial waveform 410 as shown in FIG. 6(a), and applies the Fourier transform to obtain the frequency distribution (spectrum) 510. FIG. 6(c) illustrates the spectrum 510a obtained by extracting the range of ±3 kHz on the horizontal axis as shown in FIG. 6(b). In FIGS. 6(b) and 6(c), the horizontal axis represents a frequency [kHz], and the vertical axis represents intensity [mT/m].

According to those figures, it is found that the frequency distribution (spectrum) 510 obtained by the Fourier transform of the initial waveform 410 shows a concentration into the range equal to or lower than 1 kHz.

Figure 6:
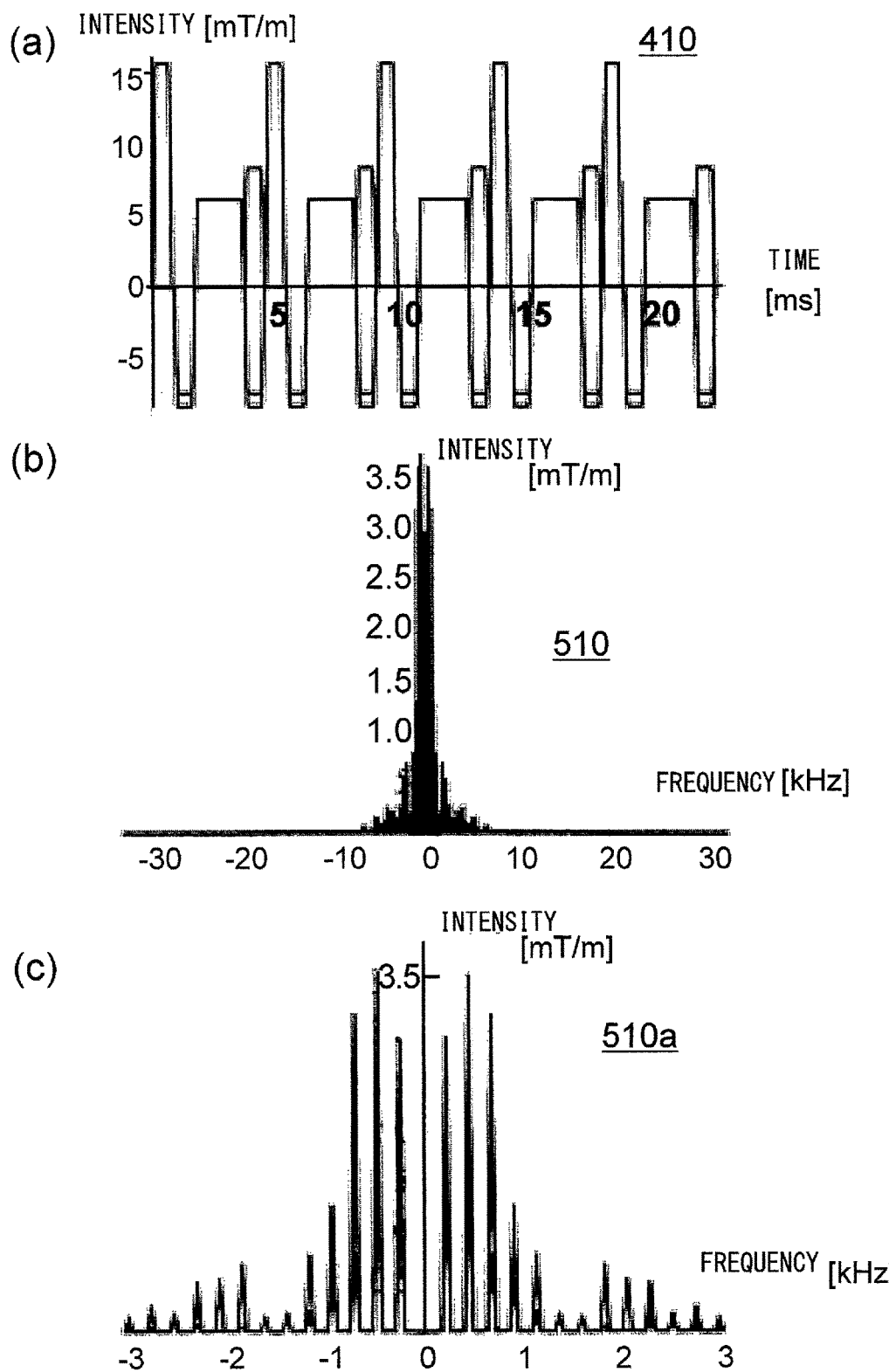
FIG. 6(a) illustrates a gradient magnetic field waveform targeted for the waveform adjustment in an embodiment of the present invention.
FIGS. 6(b) and 6(c) illustrate frequency distributions of the gradient magnetic field targeted for the waveform adjustment.
Figure 7:
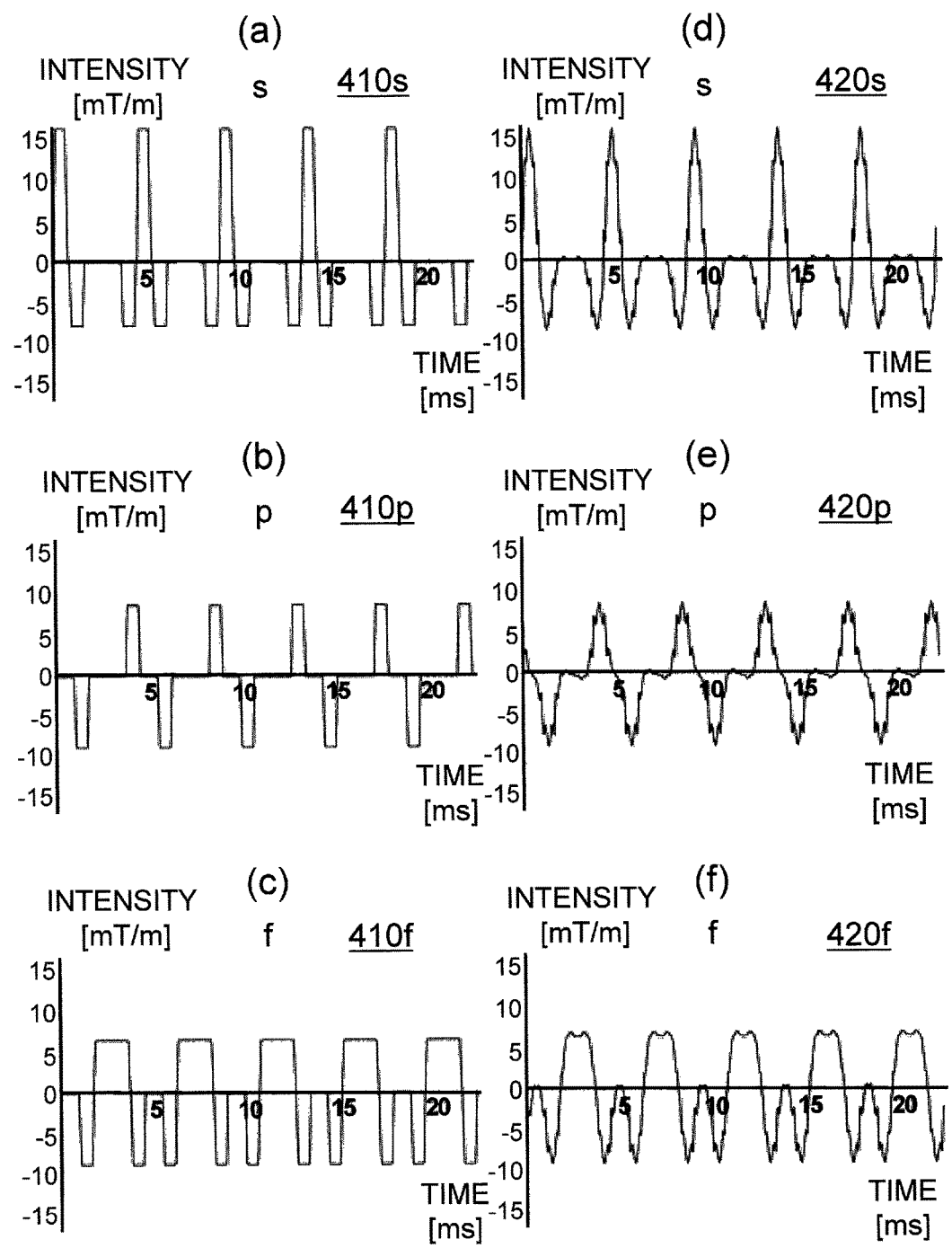
FIGS. 7(a) to 7(c) illustrate initial waveforms and FIGS. 7(d) to 7(f) illustrate filtered waveforms as an embodiment of the present invention.
Figure 8:
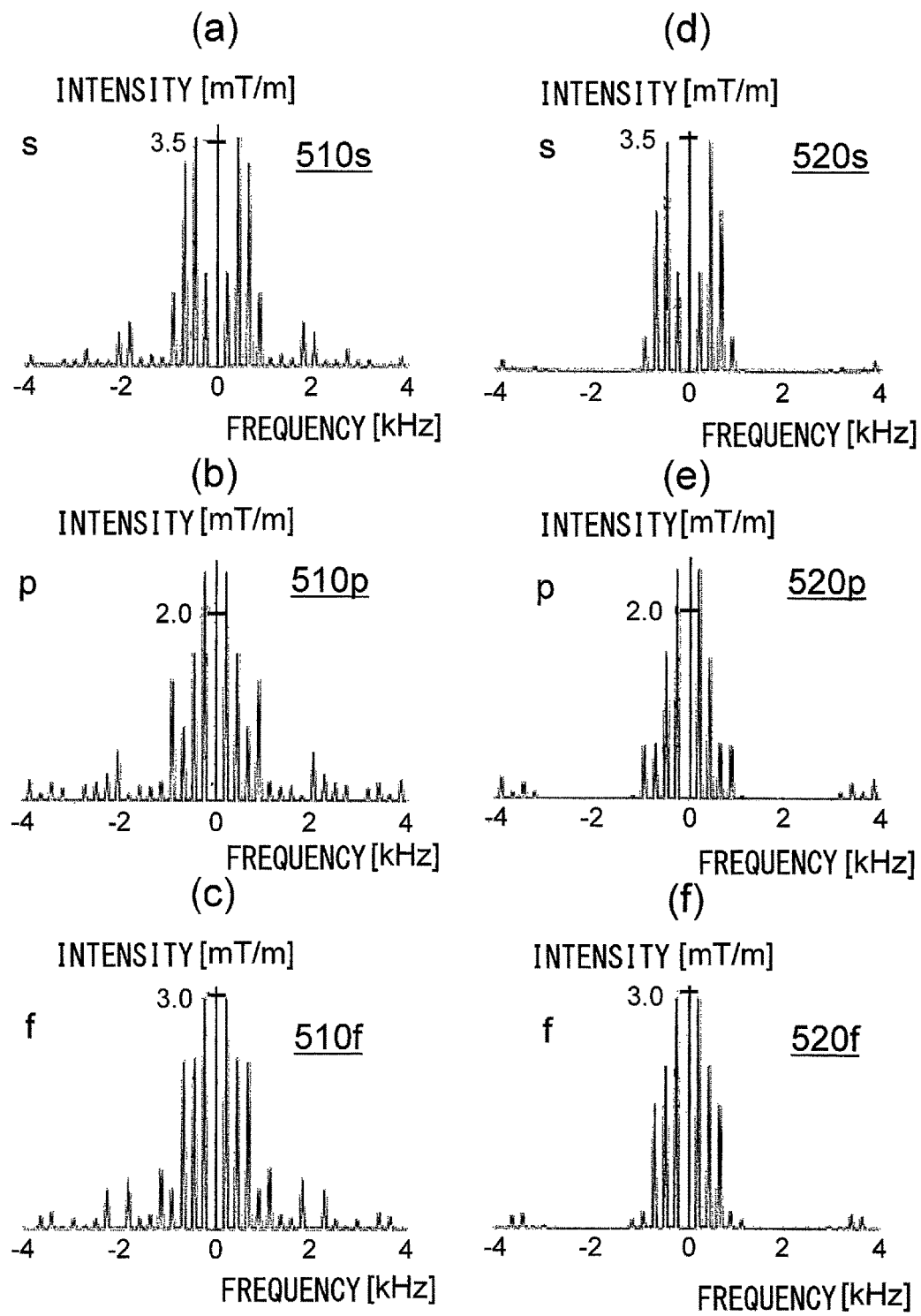
FIGS. 8(a) to 8(c) illustrate frequency distributions of the initial waveforms and FIGS. 8(d) to 8(f) illustrate the frequency distributions of the filtered waveforms as an embodiment of the present invention.

FIGS. 7(a) to 7(c) illustrate the initial waveforms 410s, 410p, and 410f which are obtained by separating the initial waveform 410 as shown in FIG. 6(a), respectively into the s, p, and f axial directions. FIGS. 8(a) to 8(c) illustrate the spectra 510s, 510p, and 510f obtained by separating the spectrum 510 as shown in FIG. 6 (c) respectively into the s, p, and f axial directions.

[Step S1102]

Figure 9:
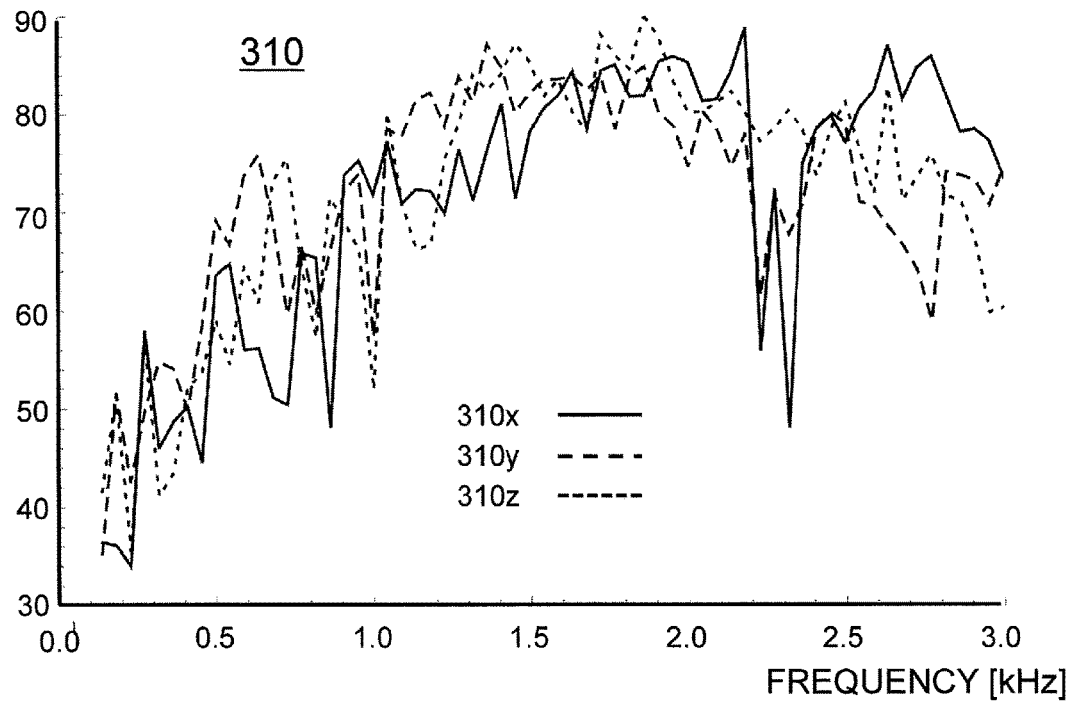
FIG. 9 illustrates examples of a response function as an embodiment of the present invention.

Firstly, there will be described the response function that is calculated in advance. In the present embodiment, the response function is calculated according to the aforementioned method, as to each of the x, y, and z axes. FIG. 9 shows one example of the response function 310 being calculated. In this figure, the graph 310x represents the response function in the x-direction, the graph 310y represents the response function in the y-direction, and the graph 310z represents the response function in the z-direction.

As illustrated, components of the response functions 310x, 310y, and 310z inherent to the MRI device 100, have the highest level at frequencies around 1.5 kHz, and extremely low level at frequencies equal to or less than 200 Hz. Therefore, if a low-pass filter is used to reduce the frequency components of the gradient magnetic field waveforms at frequencies higher than 200 Hz, the sound may become smaller.

The band-rejection section 141 multiplies the frequency distributions 510s, 510p, and 510f of the gradient magnetic fields respectively in the s, p, and f axial directions, by the response functions 310x, 310y, and 310z, in the x, y, and z axial directions as shown in FIG. 9, thereby obtaining sound pressure levels, respectively. If an imaging plane is defined in advance, the sound pressure level may be calculated only as to the application direction that is determined by this imaging plane.

Figure 10:
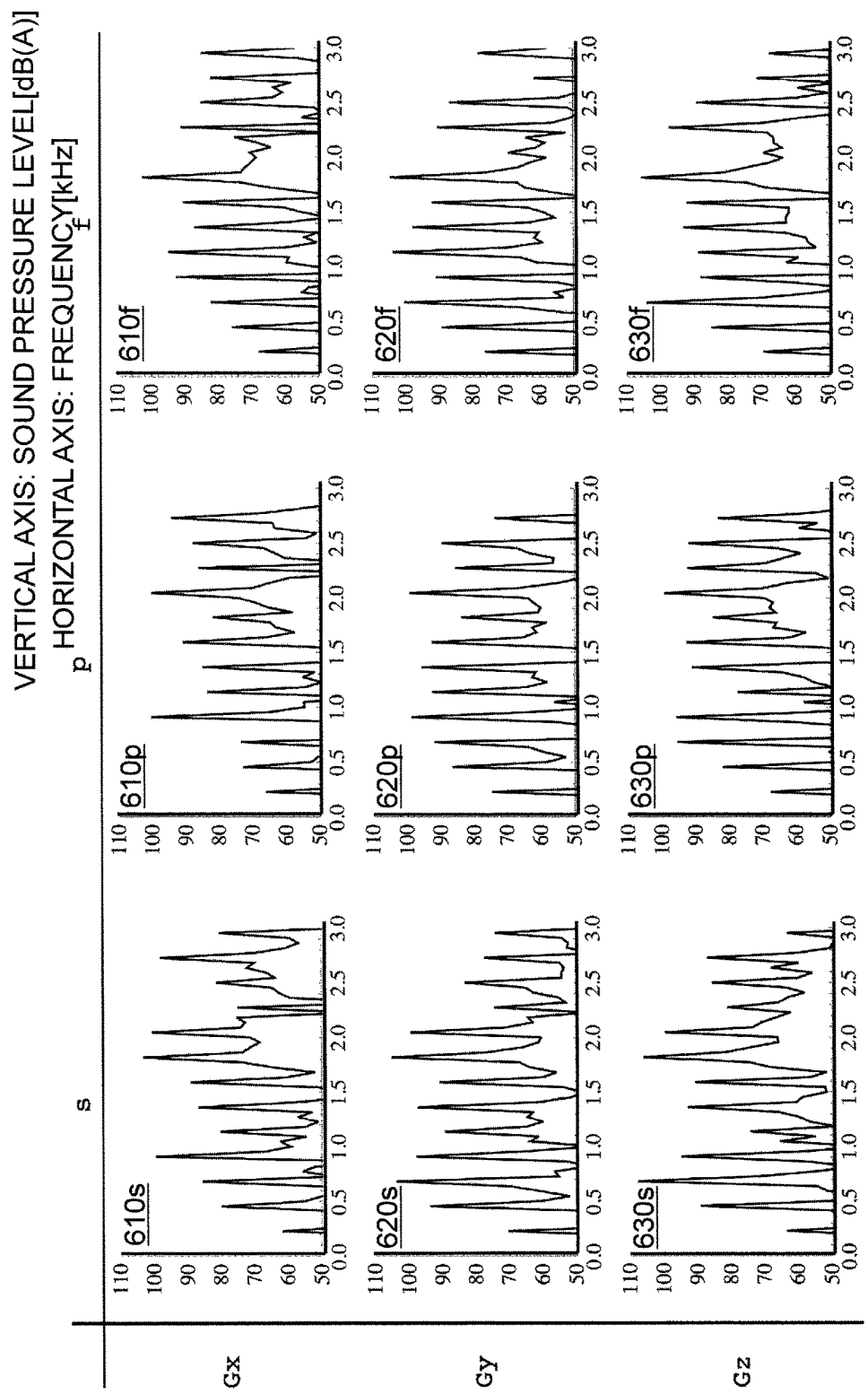
FIG. 10 illustrates sound pressure levels in respective axial directions of the initial waveform as an embodiment of the present invention.

FIG. 10 illustrates the sound pressure levels calculated as to all the axes. In each graph, the horizontal axis represents the frequency [kHz], and the vertical axis represents the sound pressure level [dB (A)].

The graph 610s indicates the sound pressure level (a product of the spectrum 510s and the response function 310x), when the slice gradient magnetic field s is applied to the x-axis (Gx). The graph 610p indicates the sound pressure level (a product of the spectrum 510p and the response function 310x), when the phase encoding gradient magnetic field p is applied to the x-axis (Gx). The graph 610f indicates the sound pressure level (a product of the spectrum 510f and the response function 310x), when the frequency encoding gradient magnetic field f is applied to the x-axis (Gx). The graph 620s indicates the sound pressure level (a product of the spectrum 510s and the response function 310y), when the slice gradient magnetic field s is applied to the y-axis (Gy). The graph 620p indicates the sound pressure level (a product of the spectrum 510p and the response function 310y), when the phase encoding gradient magnetic field p is applied to the y-axis (Gy). The graph 620f indicates the sound pressure level (a product of the spectrum 510f and the response function 310y), when the frequency encoding gradient magnetic field f is applied to the y-axis (Gy). The graph 630s indicates the sound pressure level (a product of the spectrum 510s and the response function 310z), when the slice gradient magnetic field s is applied to the z-axis (Gz). The graph 630p indicates the sound pressure level (a product of the spectrum 510p and the response function 310z), when the phase encoding gradient magnetic field p is applied to the z-axis (Gz). The graph 630f indicates the sound pressure level (a product of the spectrum 510f and the response function 310z), when the frequency encoding gradient magnetic field f is applied to the z-axis (Gz).

As seen from FIG. 10, even when any of the gradient magnetic fields s, p, and f is applied to any of the axial directions, x, y, and z, it is found that the frequency range where the sound pressure level is high is around 0.5 kHz to 1.0 kHz, and around 2 kHz. Therefore, when the phase-compensation type GE sequence 200 is executed in this MRI device 100, it is considered as effective to apply a band-pass filter that reduces those frequency bands for noise reduction.

It should be noted that as shown in FIG. 6(c), the frequency band from 0.5 kHz to 1.0 kHz occupies a large part of the spectrum 510. Therefore, intensive reduction of this band may cause considerable change of the gradient magnetic field waveform. Accordingly, a band-stop filter which reduces only the range around 2 kHz, without reducing the other range may be employed.

In other words, in the pulse sequence used for imaging, the frequency band of the gradient magnetic field where the sound pressure level is high, which is calculated by using the response function 310, is included in the range from 0 to 3 kHz. And in particular, when the pulse sequence is the phase-compensation type GE sequence 200, that frequency band may correspond to around 2 kHz. In addition, its half value width is nearly 2 kHz. Therefore, it is preferable that the band-rejection section 141 use the band-stop filter for the frequency band from 0 to 3 kHz, in particular, around 2 kHz with the half value width nearly 2 kHz, so as to filter out the frequency band of the gradient magnetic field.

Figure 11:
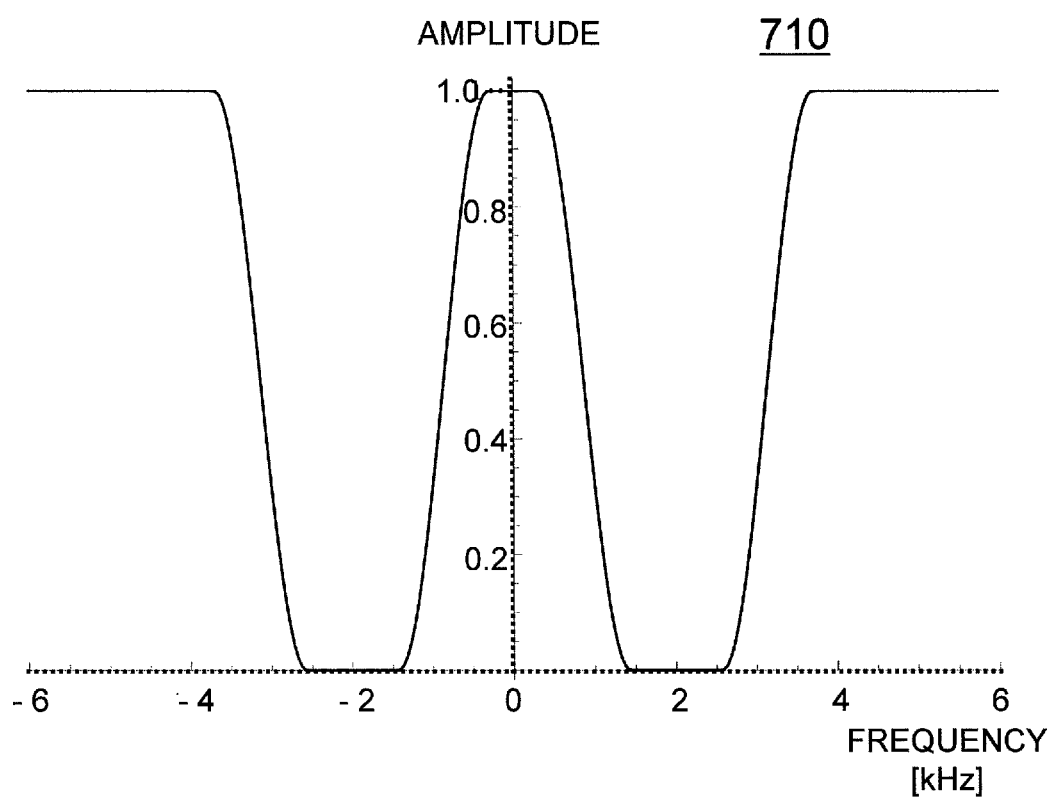
FIG. 11 illustrates an example of a band-stop filter as an embodiment of the present invention.

FIG. 11 shows one example of the band-stop filter 710 that reduces the range around 2 kHz. This band-stop filter 710 has a function obtained by subtracting from 1, a Tukey window function (maximum value is 1) with the center ±2 kHz and the half value width 1.7 kHz.

Each of the spectra 510s, 510p, and 510f as shown in FIGS. 8(a) to 8(c) is multiplied by this band-stop filter 710, and FIGS. 8(d) to 8(f) show thus obtained frequency distributions 520s, 520p, and 520f.

[Step S1104]

FIGS. 7(d) to 7(f) illustrate filtered waveforms 420s, 420p, and 420f, respectively, which are obtained by applying the inverse Fourier transform to the frequency distributions 520s, 520p, and 520f to reconstitute the waveforms.

Figure 12:
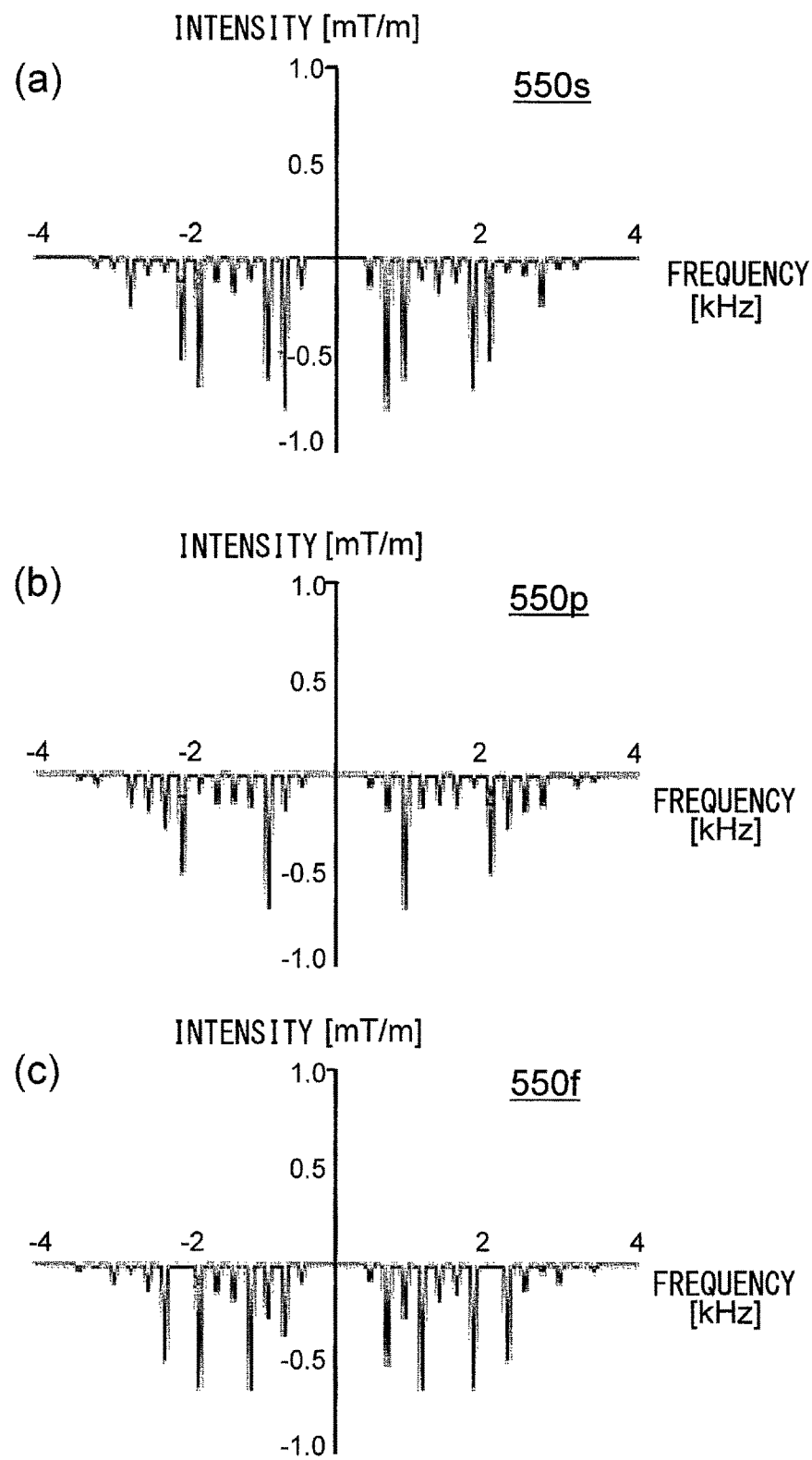
FIGS. 12(a) to 12(c) each illustrates a difference of frequency distributions between before and after applying the band-stop filter as an embodiment of the present invention.

FIGS. 12(a) to 12(c) show differences 550s, 550p, and 550f, respectively between the spectra 510s, 510p, and 510f before the band-stop filter 710 is applied (initial waveforms) and the spectra 520s, 520p, and 520f after the band-stop filter 710 is applied (filtered waveforms).

As shown in FIGS. 7(a) to 7(f), by applying the band-stop filter 710, it is found that the gradient magnetic fields keep forms approximately equivalent to the original forms, respectively, even though there are some variations.

According to a comparison between the spectra 510s, 510p, and 510f as shown in FIGS. 8(a) to 8(c), and the spectra 520s, 520p, and 520f as shown in FIGS. 8(d) to 8(f), it is found that the frequency distribution is considerably reduced in intensity, in the range around 2 kHz, by applying the band-stop filter 710. In addition, the differences 550s, 550p, and 550f as shown in FIGS. 12(a) to 12(c), indicate that the range around 1.0 kHz is also reduced not a little, where the sound pressure level is high in the initial waveforms.

[Step S1105]

The filtered waveforms 420s, 420p, and 420f as shown in FIGS. 7(d) to 7(f) may not satisfy the imaging conditions, if no modifications are applied thereto. Therefore, the waveform shaper 142 shapes the waveforms, in such a manner that those waveforms satisfy the imaging conditions as described above.

Figure 13:
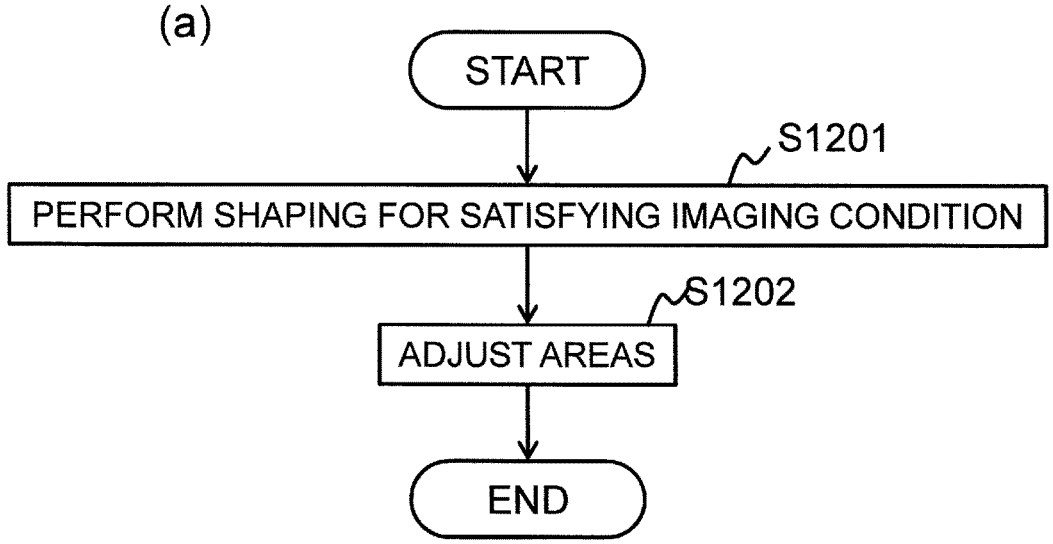
FIG. 13(a) is a flowchart showing a waveform shaping process as an embodiment of the present invention.
FIG. 13(b) is a flowchart showing the waveform shaping process as a modification example 1 of the present invention.
Figure 13:
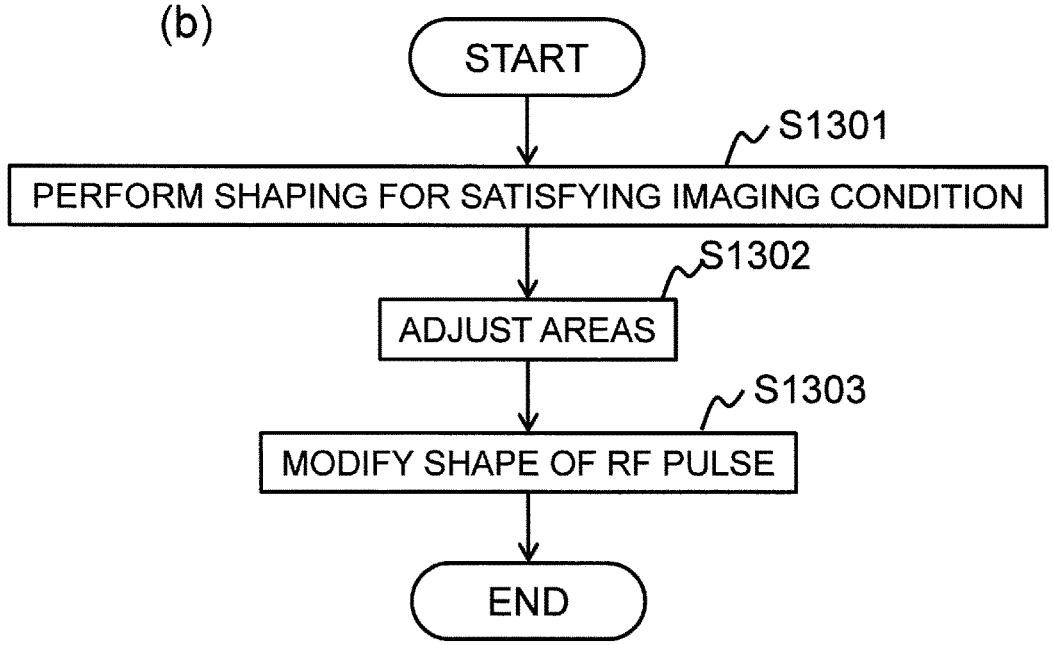

FIG. 13 (a) shows a flowchart of a waveform shaping process according to the waveform shaper 142. In the following, filtered waveforms of the trapezoid waves As0, Ap0, Af0, Bs0, Bp0, Bf0, Cs0, Cf0, Cp0, Ds0, Dp0, and Df0, which are applied to the four zones A, B, C, and D as shown in FIG. 4(a), will be respectively represented by Asd, Apd, Afd, Bsd, Bpd, Bfd, Csd, Cpd, Cfd, Dsd, Dpd, and Dfd.

The waveform shaper 142 firstly shapes the filtered waveforms, so that they satisfy the imaging conditions (step S1201). That is, the initial waveforms during the RF period and the A/D period are reconstituted as the filtered waveforms in the same periods, respectively.

Specifically, following three steps are performed.

1-1) Intensity and shape of the slice gradient magnetic field pulse Asd during the RF period are rendered the same as those of the initial waveform As0 during the same period, and the intensity of the slice gradient magnetic field pulse Csd during the A/D period is rendered zero. Then, the resultant pulses are represented by Ase and Cse, respectively.

1-2) Intensity of the phase encoding gradient magnetic field pulses Apd during the RF period and Cpd during the A/D period are rendered zero.

1-3) Intensity of the frequency encoding gradient magnetic field pulse Afd during the RF period is rendered zero. In addition, the intensity and shape of the frequency encoding gradient magnetic field pulse Cfd during the A/D period are made equal to those of the initial waveform Cf0 during the same period, and it is represented by Cfe.

Next, the waveform shaper 142 renders the summation of the areas (signed) of the filtered waveforms in the axial directions, equal to the summation of the areas (signed) of the initial waveforms in the same axial directions (step S1202). At this time, adjustment is performed only by adjusting the intensity on the pulse basis, and the application time is not changed. In addition, the intensity of the pulses during the RF period and the intensity thereof during the A/D period (Ase and Cfe) are not changed, either. This is because a slice profile and a readout condition have to be maintained the same as the initial waveform. Variations of the readout condition may cause change of a field of view and/or space resolution in the readout direction.

The phase-compensation type GE sequence 200 is designed in such a manner that a time integral value of the gradient magnetic fields in the respective axes becomes zero. Therefore, specifically, the following three steps are performed.

2-1) Intensity of Bsd and Dsd is adjusted in such a manner that the time product value of the pulses Ase, Bsd, and Dsd of the slice gradient magnetic field s becomes zero, and the adjusted Bsd and Dsd are represented by Bse and Dse.

2-2) The areas of Bp0 and Dp0 of the initial waveform are reconstituted as the areas of the pulses Bpd and Dpd of the phase encoding gradient magnetic field p, and they are represented by Bpe and Dpe.

2-3) Intensity of Bfd and Dfd is adjusted so that a time integral value of the pulses Bfd, Cfe, and Dfd of the frequency encoding gradient magnetic field f becomes zero, and the adjusted intensity is represented by Bfe and Dfe.

Figure 14:
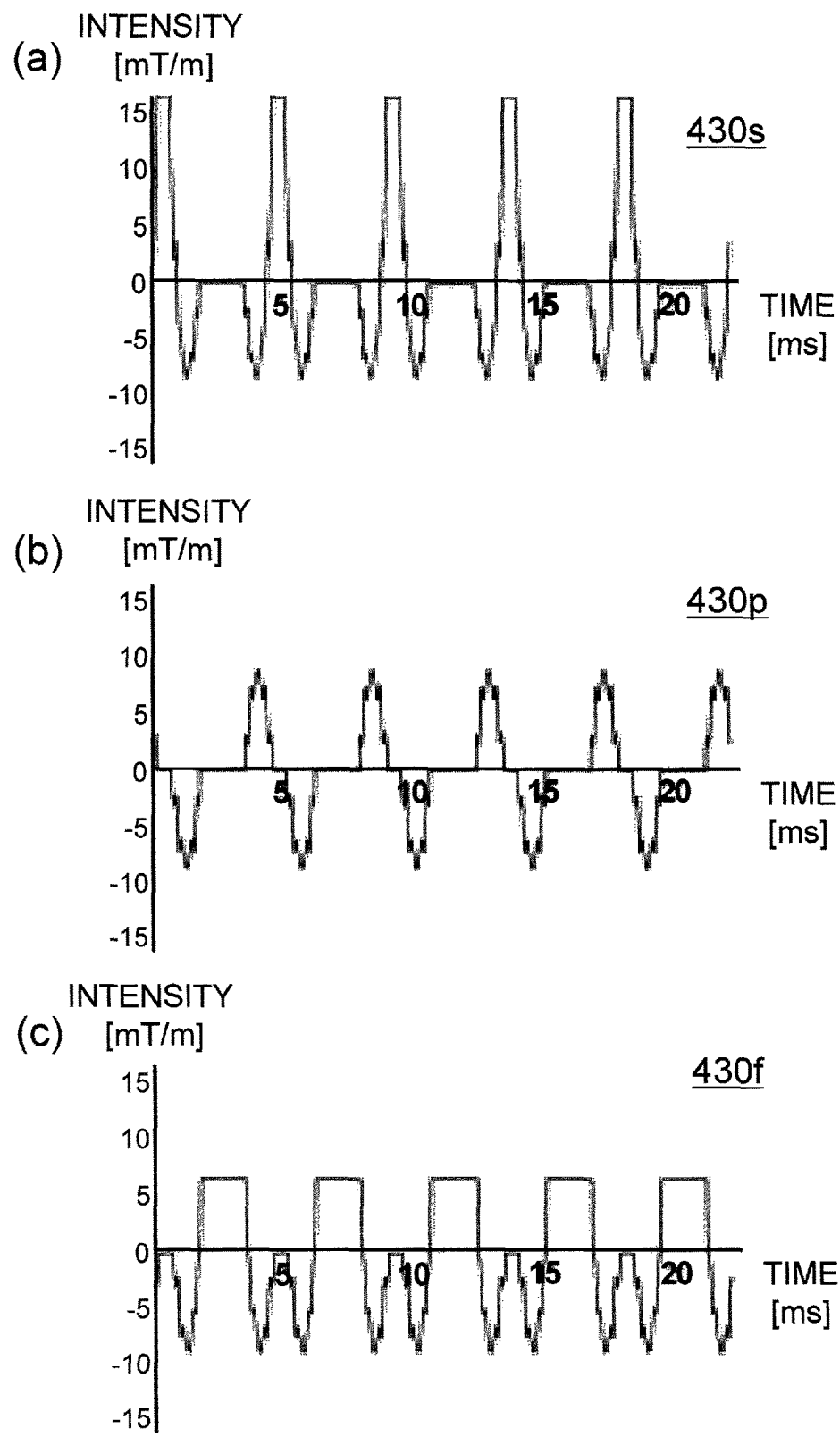
FIGS. 14(a) to 14(c) illustrate adjusted waveforms as an embodiment of the present invention.
Figure 15:
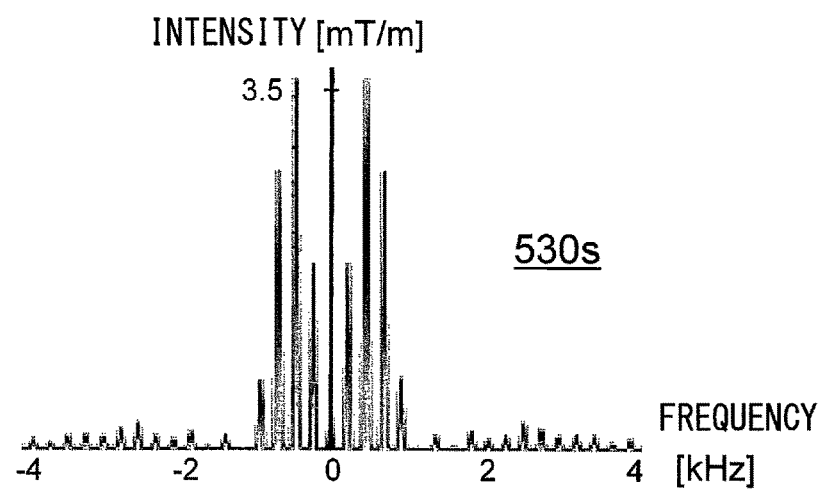
FIGS. 15(a) to 15(c) illustrate frequency distributions of the adjusted waveform as an embodiment of the present invention.
Figure 15:
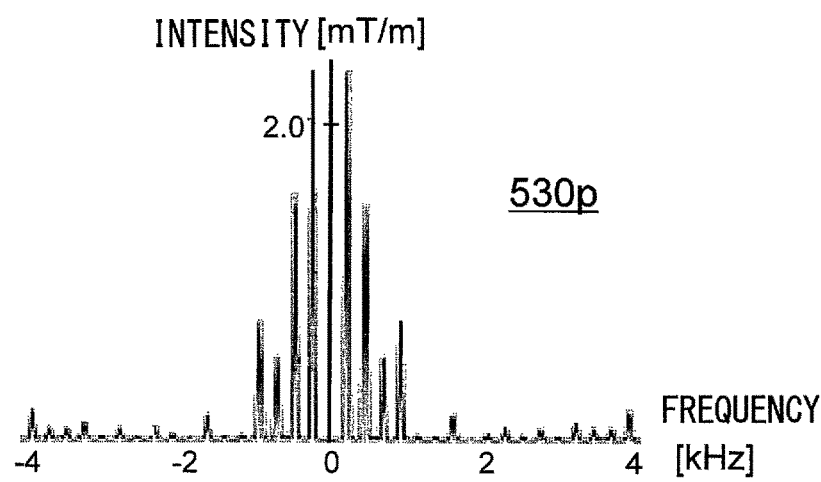
Figure 15:
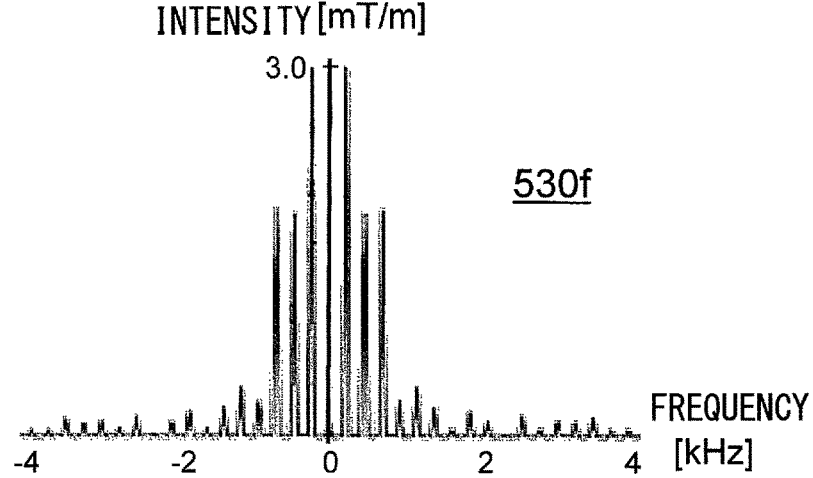

FIGS. 14(a) to 14(c) show the gradient magnetic field waveforms (adjusted waveforms) 430s, 430p, and 430f, respectively in the s, p, and f axial directions, which are obtained by shaping the filtered waveforms 420s, 420p, and 420f as shown in FIGS. 7(d) to 7(f). FIGS. 15(a) to 15(c) show the frequency distributions 530s, 530p, and 530f of the adjusted waveforms 430s, 430p, 430f respectively in the s, p, and f axial directions. In addition, FIGS. 16(a) to 16(c) shows the differences 560s, 560p, and 560f, between the frequency distributions 510s, 510p, and 510f of the initial waves respectively in the s, p, and f axial directions, and the frequency distributions 530s, 530p, and 530f of the adjusted waveforms.

Figure 16:
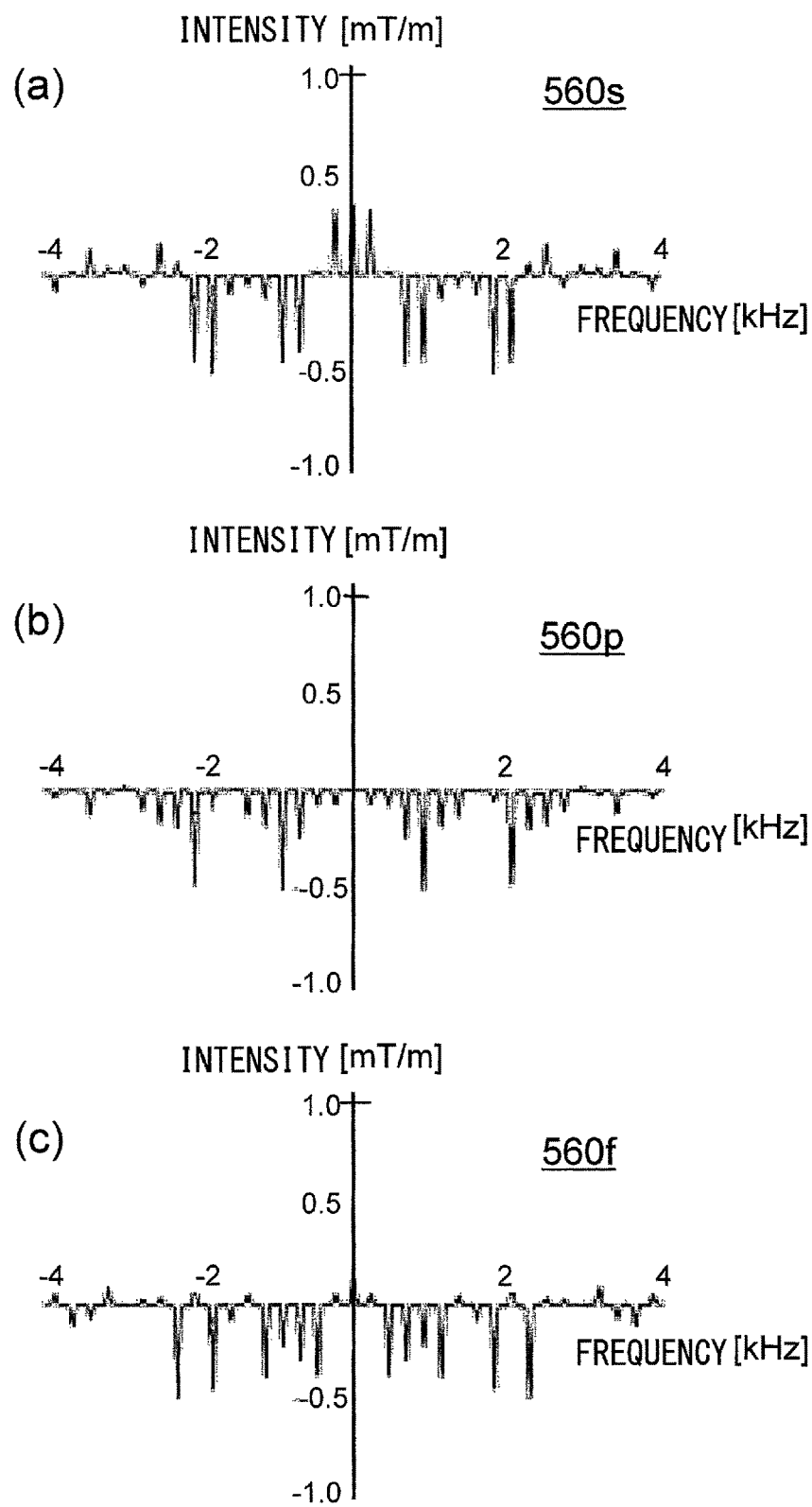
FIGS. 16(a) to 16(c) each illustrates a difference of frequency distributions between the initial waveform and the adjusted waveform as an embodiment of the present invention.

When the differences 560s, 560p, and 560f as shown in FIGS. 16(a) to 16(c) are compared with the differences 550s, 550p, and 550f, between before and after applying the filter as shown in FIGS. 12(a) to 12(c), it is found that components around 2 kHz and around 1 kHz are still lowered, even a degree of intensity reduction becomes smaller.

[Variation of Sound Pressure Level]

Finally, there will be described how the sound pressure level varies according to the gradient magnetic field waveform adjusting process of the present embodiment.

Figure 17:
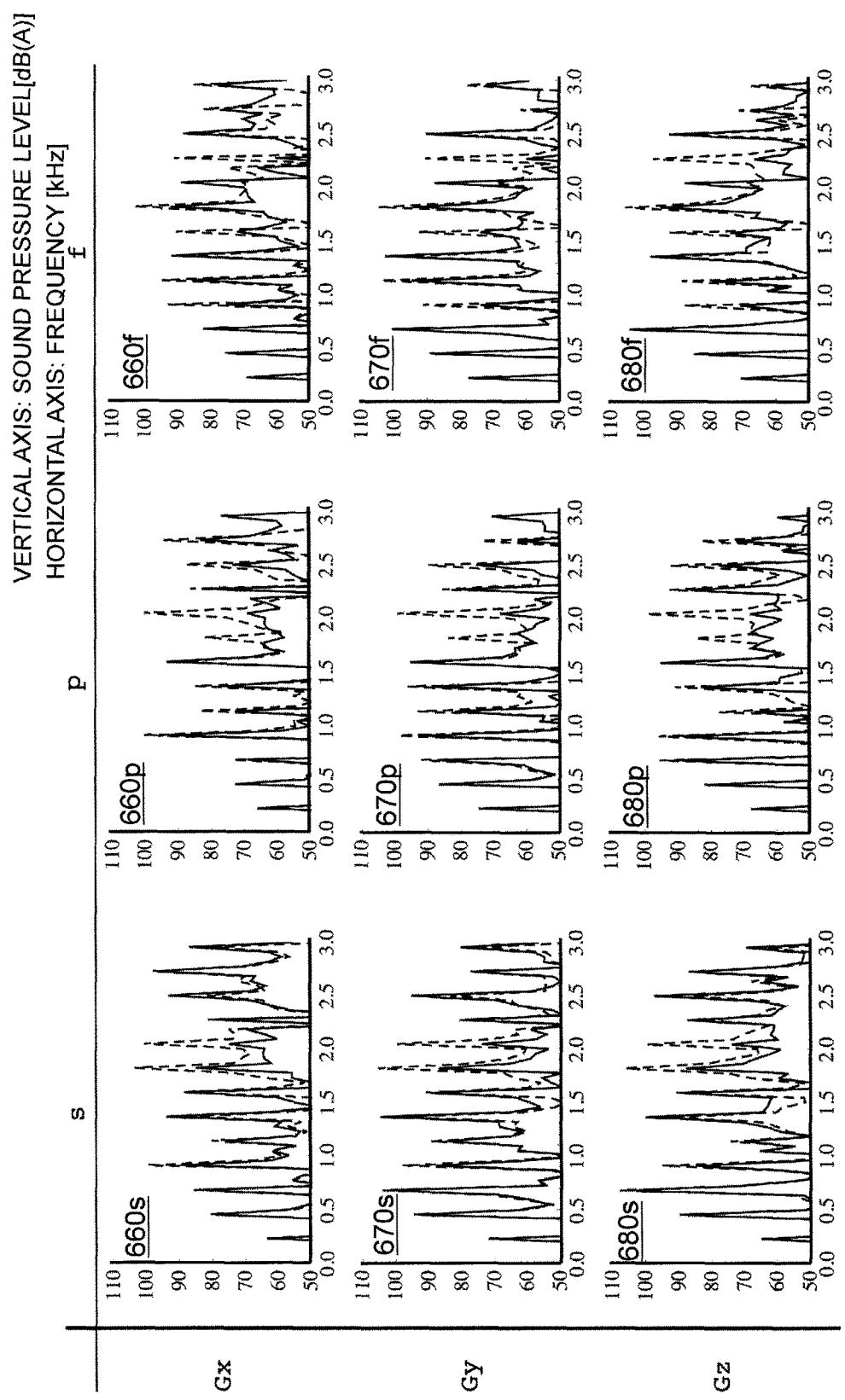
FIG. 17 illustrates sound pressure levels in the respective axial directions of the adjusted waveforms as an embodiment of the present invention.

FIG. 17 shows the sound pressure levels of the adjusted waveforms, obtained by the band filtering using the band-stop filter 710 and the waveform shaping thereafter. The sound pressure levels are obtained by multiplying the frequency distributions 530s, 530p, and 530f of the adjusted waveforms respectively in the s, p, and f axial directions, by the response functions 310x, 310y, and 310z in the x, y, and z axial directions. In the following, those are represented by Gx, Gy, and Gz.

In this figure, the sound pressure levels 660s, 660p, 660f, 670s, 670p, 670f, 680s, 680p, and 680f of the adjusted waveforms are represented by the solid lines. For comparison, the sound pressure levels 610s, 610p, 610f, 620s, 620p, 620f, 630s, 630p, and 630f respectively in the same axial directions, before applying the band-stop filter 710, that is, the sound pressure levels of the initial waveforms as shown in FIG. 10, are represented by the dotted lines.

According to the gradient magnetic field waveform adjusting process including the band-rejection process by using the band-stop filter 710 of the present embodiment, similar to FIGS. 16(a) to 16(c), it is confirmed that the sound pressure level is reduced at the frequencies around 2 kHz and around 1 kHz on any of the axes.

The results above will be shown by numerical values.

The table 810 in FIG. 18(a) shows summations (Overall) respectively of the aforementioned sound pressure levels 610s, 610p, 610f, 620s, 620p, 620f, 630s, 630p, and 630f, before applying the band-stop filter 710 (of the initial waveforms). The unit of each value is [dB].

The table 820 in FIG. 18(b) also shows summations (Overall) respectively of the aforementioned sound pressure levels 660s, 660p, 660f, 670s, 670p, 670f, 680s, 680p, and 680f of the adjusted waveforms after applying the band-stop filter 710 and shaping.

The table 830 in FIG. 18(c) shows differences between FIG. 18(a) and FIG. 18(b).

It is seen from the table 830 as shown in FIG. 18(c), the sound pressure levels are reduced, by 3 dB to 7 dB, when the gradient magnetic fields respectively of the s, p, and f axes are applied to any of the x, y, and z axes.

As described above, the MRI device of the present embodiment is provided with the gradient magnetic field waveform adjuster 140 configured to adjust the initial waveform, being the waveform of the gradient magnetic field predefined in the pulse sequence, and to obtain an adjusted waveform, and the pulse sequence is used to irradiate the test subject 103 placed in a static magnetic field, with a high-frequency magnetic field according to the predetermined imaging condition, along with applying the gradient magnetic field thereto, and to obtain echo signals generated from the test subject 103. The gradient magnetic field waveform adjuster 140 is provided with the band-rejection section 141 configured to filter out a part of the frequency band of the initial waveform, and to generate a filtered waveform, and a waveform shaper 142 configured to shape the filtered waveform in such a manner that the imaging condition is satisfied, so as to obtain the adjusted waveform. The echo measurement section 120 is further provided, configured to measure echo signals according to the imaging condition and the pulse sequence, and the echo measurement section 120 applies the adjusted waveform to the pulse sequence and measures the echo signals.

According to the present embodiment, the band-stop filter 710 is applied to the gradient magnetic field, and thereafter, the waveform is shaped. The band-stop filter 710 is designed in such a manner that a frequency band having the sound pressure level equal to or higher than a threshold is reduced, on the basis of the sound pressure level obtained from a result of actual measurement. In addition, the gradient magnetic field waveform after the band is reduced by the band-stop filter 710 is shaped so that the imaging conditions are satisfied.

In the adjusted waveform obtained by the processes above, as shown in FIG. 17, the sound pressure level is lowered, compared to the initial waveform. In addition, the imaging conditions are satisfied. Furthermore, since the waveform shaping is carried out only by intensity, there is no possibility that the time for applying the gradient magnetic field is extended. Therefore, according to the present embodiment, it is possible to reduce the sound pressure level and to achieve noise reduction, without extending the application time of the gradient magnetic field nor deteriorating an image quality.

Accordingly, the present embodiment allows effective reduction of the sound pressure level, even in the imaging sequence that does not have sufficient pulse intervals.

Modification Example 1

According to the aforementioned embodiment, in the waveform shaping process, the initial waveforms are reconstituted as the gradient magnetic field waveforms in the RF period and in the A/D period. However, the waveform shaping process is not limited to this method. By way of example, a degree of flexibility is enhanced, and the shaping of the gradient magnetic field waveforms during those periods may be configured in such a manner that only average values of intensity are equalized.

In other words, the waveform shaper 142 may perform shaping of the filtered waveforms, so that the average intensity of the filtered waveform during the irradiation of high-frequency magnetic field and the average intensity of the filtered waveform during A/D, become approximately equal to the average intensity of the initial waveforms during the same periods, respectively, so as to obtain the adjusted waveform.

In this situation, the gradient magnetic field during the RF period becomes inconsistent. Therefore, also for the RF pulse 202, the waveform of the RF pulse is modified, in conformity with the slice gradient magnetic field waveform after shaping, so that a slice thickness and a slice profile are not changed from the initial state. In other words, the waveform shaper 142 performs shaping of the waveform of the RF pulse, in such a manner that variation of the slice profile due to the adjusted waveform is reduced.

In addition, the intensity of the gradient magnetic field during the A/D period also becomes inconsistent. Thus, echo signals after sampling may fail to be arranged at equal intervals in the k-space. Accordingly, the arrangement in the k-space is made equal intervals by gridding, and thereafter, the Fourier transform is applied so as to reconstruct an image. In other words, the image reconstructor 130 performs gridding of the echo signals in accordance with the adjusted waveform during the time the echo signals are measured, and thereafter, reconstructs an image.

Now, FIG. 13(b) shows the waveform shaping procedure of the present modification example. The gradient magnetic fields targeted for the waveform shaping are represented by Asd, Bsd, Bpd, Bfd, Cfd, Dsd, Dpd, and Dfd, obtained by the band-rejection process where the band-stop filter 710 is applied to the initial waveforms as shown in FIGS. 4(a) to 4(c).

The waveform shaper 142 performs shaping of the filtered waveforms and the RF waveform, in such a manner that the imaging conditions are satisfied (step S1301). In this shaping, only the intensity is adjusted, without changing the application time.

Specifically, following steps are performed;
3-1) An average intensity value of the slice gradient magnetic field pulse Asd during the RF period is equalized to the average intensity value of the initial waveform As0 during the same period, and the intensity of the slice gradient magnetic field pulse Csd during the A/D period is rendered zero. The processed waveform in the zone A is represented by Asg.
3-2) Intensity of the phase encoding gradient magnetic field pulses Apd and Cpd during the RF period and the A/D period are rendered zero.
3-3) Intensity of the frequency encoding gradient magnetic field pulse Afd during the RF period is rendered zero, and an average value of the intensity of the frequency encoding gradient magnetic field pulse Cfd during the A/D period is equalized to the average intensity value of the initial waveform Cf0 during the same period. The processed waveform in the zone C is represented by Cfg.

The waveform shaper 142 equalizes the summation of the areas (signed) of the filtered waveform in each axis direction, to the summation of the areas (signed) of the initial waveform in the same axis direction (step S1302). In this situation, only the intensity per pulse is adjusted, without changing the application time.

Specifically, following steps are performed;
4-1) Intensity of Bsd and Dsd is adjusted in such a manner that a summation of the areas (signed) of the slice gradient magnetic field pulses Asg, Bsd, and Dsd becomes equal to the summation of the areas (singed) of As0, Bs0, and Ds0, and the adjusted intensity is represented by Bsg and Dsg.
4-2) Intensity of Bpd and Dpd is adjusted in such a manner that the areas of the phase encoding gradient magnetic field pulses Bpd and Dpd become equal to the areas of the initial waveforms of Bp0 and Dp0, respectively, and they are represented by Bpg and Dpg.
4-3) Intensity of Bfd and Dfd is adjusted in such a manner that a summation of the areas (signed) of the frequency encoding gradient magnetic field pulses Bfd, Cfg, and Dfd is equalized to the summation of the areas (signed) of Bf0, Cf0, and Df0, and they are represented by Bfg and Dfg.

Finally, the shape of the RF pulse 202 is modified to match the shape of the slice gradient magnetic field Asg (step S1303). In here, the shape of the RF pulse 202 is modified in such a manner that the slice thickness and the slice profile are not changed from the initial state, as described above.

By way of example, this modification can be achieved by the small tip angle approximation (STAA) method. Specifically, the RF pulse $b_{As3}$ satisfying the conditions above, is obtained according to the following formula (1), on the basis of the initial RF pulse $b_{As0}$ before shaping the intensity of the gradient magnetic field, i.e., the initial RF pulse set in the phase-compensation type GE sequence 200.

[Formula 1]

$$b_{As3}(t) = b_{As0}(\tau(t)) f_{As3}(t) / f_{As0}(t)$$

$$\tau(t) = \int_0^t f_{As3}(t) / f_{As0}(t) dt \quad (1)$$

where $f_{As0}$ and $f_{As3}$ represent, respectively, the gradient magnetic field intensity of the initial waveform and the gradient magnetic field intensity after shaping. A time dilation function is represented by T.

FIGS. 19(a) to 19(i) show a comparison between the adjusted waveforms after shaping the initial waveforms 400s, 400p, and 400f in FIGS. 4(a) to 4(c) according to the method of the present modification example, and the adjusted waveforms after shaping according to the method of the aforementioned embodiment.

Figure 19:
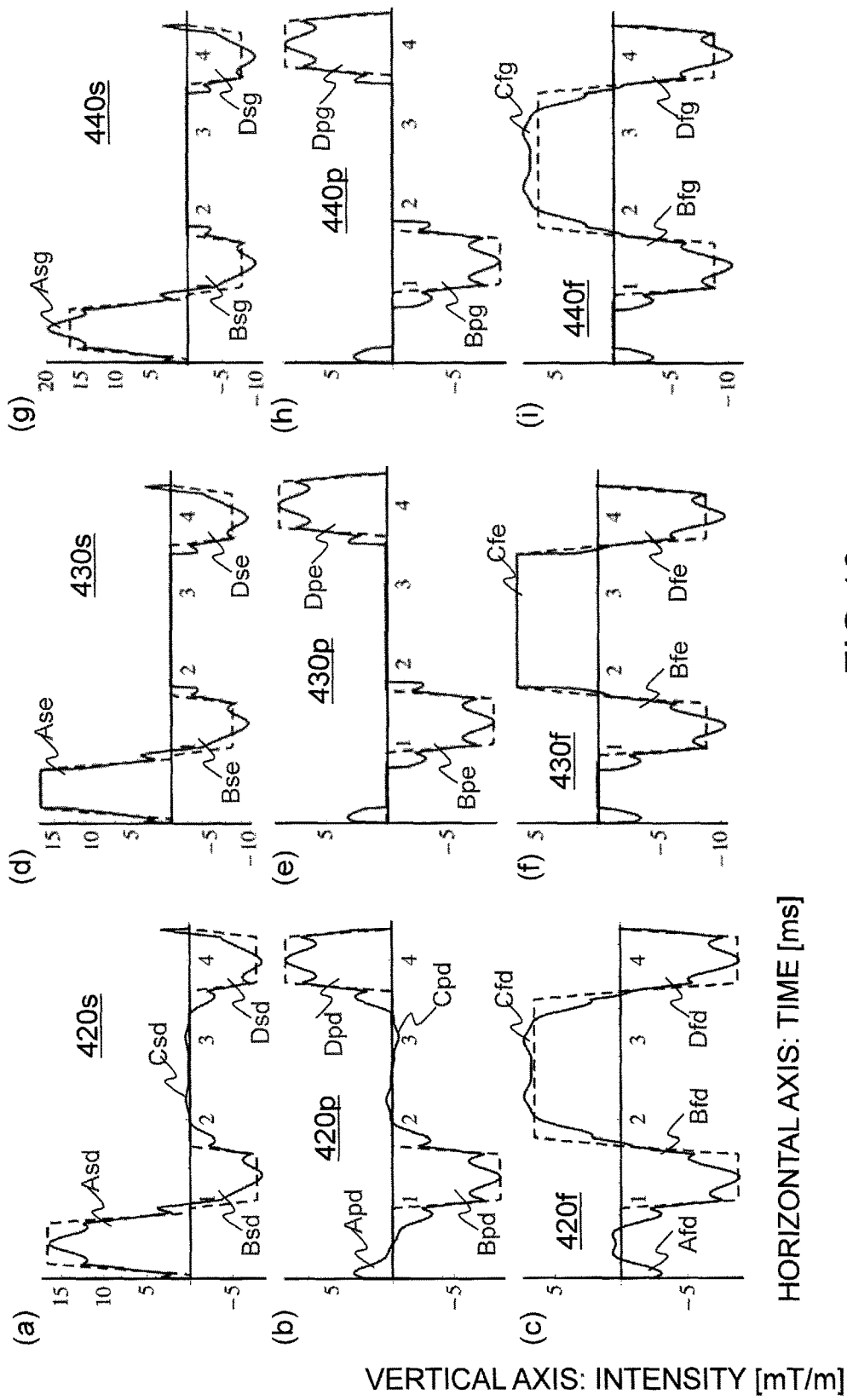
FIGS. 19(a) to 19(c) illustrate the filtered waveforms and FIGS. 19(d) to 19(f) illustrate the adjusted waveforms as an embodiment of the present invention.
FIGS. 19(g) to 19(i) illustrate the adjusted waveforms as the modification example 1 of the present invention.

In the figures, FIGS. 19(a) to 19(c) show the filtered waveforms before shaping, in the s, p, and f axis directions, that is, a part of the filtered waveforms 420s, 420p, and 420f. FIGS. 19(d) to 19(f) show a part of the adjusted waveforms 430s, 430p, and 430f in the s, p, and f axis directions, after the waveform shaping according to the aforementioned embodiment. FIGS. 19(g) to 19(i) show the adjusted waveforms 440s, 440p, and 440f in the s, p, and f axis directions, after the waveform shaping according to the present modification example. In each of the figures, the dotted lines represent the initial waveforms 400s, 400p, and 400f as shown in FIGS. 4(a) to 4(c).

The adjusted waveforms 430s, 430p, and 430f as shown in FIGS. 19(d) to 19(f) are compared with the adjusted waveforms 440s, 440p, and 440f as shown in FIGS. 19(g) to 19(i).

As for the latter case, constraints for obtaining constant gradient magnetic field pulses during the RF irradiation and during the A/D are eliminated as described above, and thus the intensity variation of the slice gradient magnetic field (Asg) in the zone A and the intensity variation of the frequency encoding gradient magnetic field (Cfg) in the zone C are not constant. This is an outstanding difference.

The table 840 in FIG. 18(d) shows differences between the sound pressure levels of the initial waveforms, and the sound pressure levels of the adjusted waveforms obtained according to the present modification example. When compared with the differences from the adjusted waveforms of the aforementioned embodiment shown in the table 830 in FIG. 18(c), it is indicated that the sound pressure levels are further reduced in the cases where the slice gradient magnetic field s is applied to the x-axis direction (Gx), and the frequency encoding gradient magnetic field f is applied to each of the axis directions.

In other words, it is found that in those cases, by eliminating the constraints for having constant gradient magnetic field intensity during the RF irradiation and during the A/D, there is an effect of sound pressure level reduction, by 2 dB or more. In particular, when the frequency encoding gradient magnetic field f is applied in the Gx-axis direction, a high reduction effect can be obtained, such as reduced more by 8 dB.

Modification Example 2

In the aforementioned embodiment, the same band-stop filter 710 (the center frequency is 2 kHz and the full width is 3.4 kHz) as shown in FIG. 11 is applied to any of the axes, and the band-rejection process is performed. However, as shown in FIG. 9, the response function 310 is different by axis. Therefore, it is possible to employ the band-stop filter provided with a band which is different by axis.

In other words, the band-rejection section 141 may employ various band-stop filters respectively for the application axes of the gradient magnetic fields, so as to filter out different frequency bands.

The table 850 in FIG. 18(e) shows differences between the sound pressure levels (Overall) of the adjusted waveforms when the band-rejection process is performed by using a band-stop filter with specifications (the center frequency is 2 kHz, and the full width is 4.2 kHz) which is different from the aforementioned band-stop filter 710, and the sound pressure levels (Overall) of the initial waveforms. In this example, the waveform shaping process is the same method as of the aforementioned embodiment.

When the sound pressure levels (Overall) in the table 850 as shown in FIG. 18(e) and the table 830 as shown in FIG. 18(c) are compared, it is found that the sound pressure level is reduced more, when the band-stop filter (the center frequency is 2 kHz and the full width is 4.2 kHz) is applied in applying the frequency encoding gradient magnetic field f to the Gx-axis direction.

Therefore, in the case where the frequency encoding gradient magnetic field f is applied to the Gx-axis direction, the center frequency of the band-stop filter is set to 2 kHz and the full width is set to 4.2 kHz. In the other case, the center frequency of the band-stop filter is set to 2 kHz, and the full width is set to 3.4 kHz. With this configuration, it is possible to obtain a much higher effect of sound pressure level reduction.

As described above, by employing the band-stop filter suitable for each axis, the sound pressure level can be reduced more.

Modification Example 3

In the aforementioned embodiment, the band-rejection process of the step S1103 using the band-stop filter 710 is performed for all the axes. However, it is not necessary to perform this band-rejection process for all the axes.

Loudness depends on the sound having the highest sound pressure level. Therefore, almost the same effect can be obtained, even when the band-rejection process is applied only to the axis having a high sound pressure level. In other words, the band-rejection section 141 may filter out only a predetermined frequency band of the gradient magnetic field that is applied to the axis direction having the sound pressure level (Overall) being a predetermined level or higher.

By way of example, in the case of the initial waveform 410 as shown in FIG. 6(a), according to the results in the table 810 of FIG. 18(a), the value of the sound pressure level (Overall) exceeds 110 dB, when the slice gradient magnetic field s is applied to the x, y, and z axis directions, and when the frequency encoding gradient magnetic field is applied to the y and z axis directions. Therefore, band-rejection process is performed only for those cases, for example.

With this configuration, it is possible to simplify the process, relative to performing the band-rejection process for all the axes. Also in this situation, various frequency bands may be filtered as to each axis, using the band-rejection process like the modification example 2.

Modification Example 4

Frequency characteristics of the gradient magnetic field waveform may vary depending on the imaging conditions such as fields of view, TR and TE. Therefore, in the aforementioned embodiment, if the imaging conditions are changed, it is necessary to perform the band-rejection process on every time of change.

However, it is possible to configure such that the band-rejection process and the waveform shaping process are performed in advance by the aforementioned method, for the pulse sequence and the imaging conditions frequently used, so as to create adjusted waveforms, and then, those adjusted waveforms may be stored in the storage unit 111, or the like, in association with the imaging conditions.

In other words, as shown in FIG. 2(b), the MRI device 100 may be provided with a database that stores the adjusted waveforms (gradient magnetic field waveforms after adjustment of noise reduction) obtained by the aforementioned method, in such a manner that the adjusted waveforms are associated with the imaging conditions and the pulse sequence used for obtaining the waveforms. Each gradient magnetic field waveform after adjustment of noise reduction is obtained by filtering out a part of the frequency band of the initial waveform being the gradient magnetic field waveform set in the pulse sequence, and thereafter shaping the waveform so that the imaging conditions are satisfied.

In this case, neither the gradient magnetic field waveform adjuster 140 nor the response function calculator 150 may be provided.

In the imaging for this case, the echo measurement section 120 measures echo signals, by applying to the pulse sequence, the adjusted waveforms (gradient magnetic field waveforms after adjustment of noise reduction) which are stored in the database in association with the user-designated imaging conditions and pulse sequence.

It is further possible to configure such that the waveform after shaping according to the aforementioned embodiment and the waveforms after shaping according to the aforementioned modification examples, may be stored, respectively, allowing the user to select any of the waveforms.

Comparative Example

Figure 20:
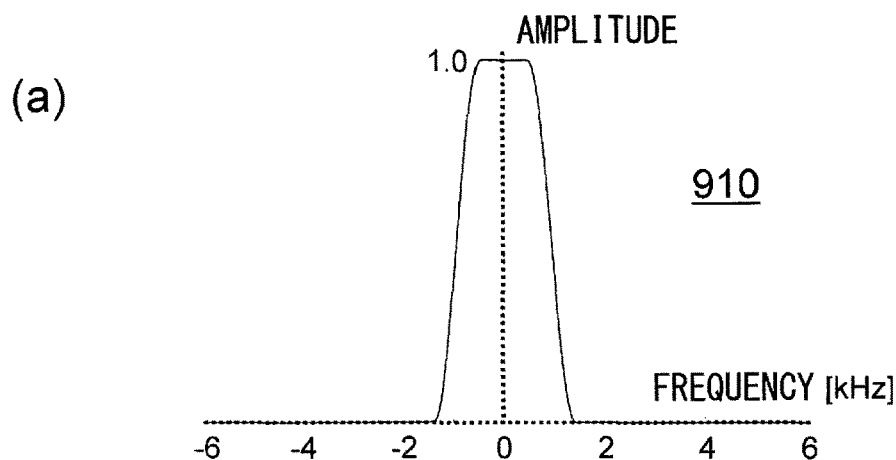
FIG. 20(a) illustrates a gradient magnetic field waveform after adjustment using a conventional low-pass filter.
FIG. 20(b) illustrates the gradient magnetic field waveforms after adjustment using the low-pass filter of FIG. 20(a)
FIG. 20(c) shows differences of the summations of the sound pressure levels between FIG. 18(a) and FIG. 20(b).
Figure 20:
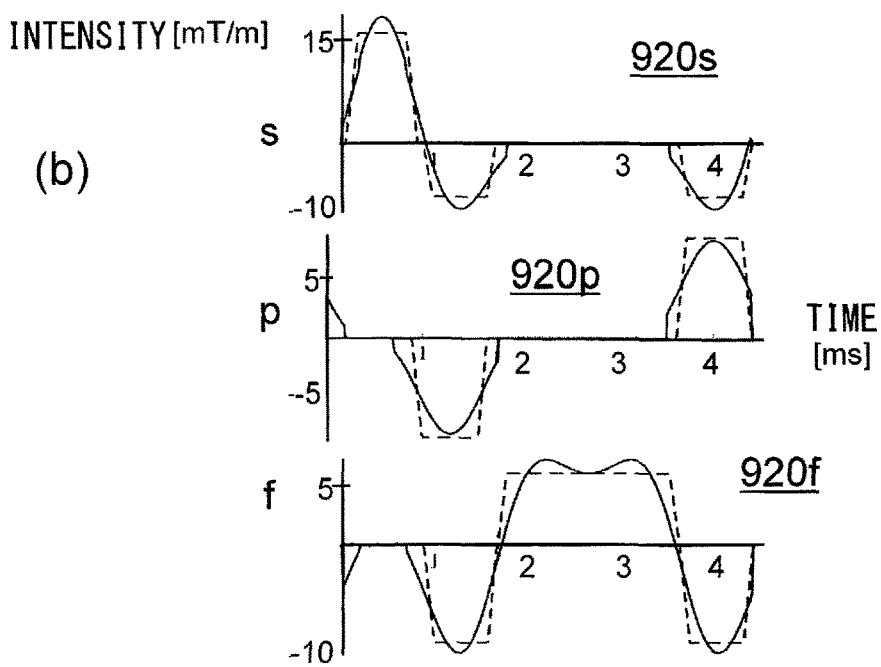

As a comparative example, FIGS. 20(a) to 20(c) show the cases where a conventional low-pass filter was used for the band-rejection process, instead of the band-stop filter 710 of the present embodiment.

FIG. 20(a) shows a low-pass filter 910 used for the band-rejection process. The band-stop filter 710 as shown in FIG. 11 reduced only the range around 2 kHz, whereas the low-pass filter 910 reduced (cuts) high-frequency components in the range equal to or higher than 2 kHz.

FIG. 20(b) shows the gradient magnetic field waveforms 920s, 920p, and 920f respectively in the s, p, and f axis directions, after filtering out by using the low-pass filter 910 and performing the waveform shaping of the aforementioned modification example. Since this low-pass filter was applied, high-frequency components were cut. Accordingly, the resultant waveform became considerably smooth, compared to the adjusted waveforms 440s, 440p, and 440f as shown in FIGS. 19(g) to 19(i).

FIG. 20(c) shows the table 930 indicating variations of the sound pressure levels (Overall) before and after shaping. When compared with the result in the table 840 as shown in FIG. 18(d), reduction of the sound pressure levels was equal or smaller. By way of example, in the case where the frequency encoding gradient magnetic field f was applied to the Gx axis direction, there was variation of −14 dB when the band-stop filter 710 was used, whereas the amount of change was −11 dB by using the low-pass filter 910, and the effect became smaller by 3 dB.

As thus described, it is found that there is a larger effect of noise reduction, when the band filtering is performed by using the band-stop filter of the present embodiment, relative to the method that uses the conventional low-pass filter 910.

The aforementioned embodiment and the modification examples have been described, with the use of the phase-compensation type GE sequence 200 as the pulse sequence, but this is not the only example.

The embodiment of the present invention is not limited to the aforementioned embodiment nor the modification examples, and various addition and modifications may be possible without departing from the scope of the invention.

DESCRIPTION OF SYMBOLS

100: MRI device, 101: magnet, 102: gradient coil, 103: test subject, 104: sequencer, 105: gradient power supply, 106: high-frequency magnetic field generator, 107: transmitter-receiver coil, 108: receiver, 109: computer, 110: monitor, 111: storage unit, 112: microphone, 113: frequency analyzer, 120: echo measurement section, 130: image reconstructor, 140: gradient magnetic field waveform adjuster, 141: band-rejection section, 142: waveform shaper, 150: response function calculator, 160: database, 200: phase-compensation type GE sequence, 201: slice gradient magnetic field, 202: RF pulse, 203: slice rephasing gradient magnetic field, 204: phase encoding gradient magnetic field, 205: dephasing frequency encoding gradient magnetic field, 206: frequency encoding gradient magnetic field, 207: echo signal, 208: gradient magnetic field, 209: gradient magnetic field, 210: gradient magnetic field, 310: response function, 310x: response function, 310y: response function, 310z: response function, 400s: initial waveform, 400p: initial waveform, 400f: initial waveform, 410: initial waveform, 410s: initial waveform, 410p: initial waveform, 410f: initial waveform, 420s: filtered waveform, 420p: filtered waveform, 420f: filtered waveform, 430s: adjusted waveform, 430p: adjusted waveform, 430f: adjusted waveform, 440s: adjusted waveform, 440p: adjusted waveform, 440f: adjusted waveform, 510: frequency distribution of initial waveform, 510a: frequency distribution of initial waveform, 510s: frequency distribution of initial waveform, 510p: frequency distribution of initial waveform, 510f: frequency distribution of initial waveform, 520s: frequency distribution of filtered waveform, 520p: frequency distribution of filtered waveform, 530f: frequency distribution of filtered waveform, 550s: difference of frequency distributions between initial waveform and filtered waveform, 550p: difference of frequency distributions between initial waveform and filtered waveform, 550f: difference of frequency distributions between initial waveform and filtered waveform, 560s: difference of frequency distributions between initial waveform and adjusted waveform, 560p: difference of frequency distributions between initial waveform and adjusted waveform, 560f: difference of frequency distributions between initial waveform and adjusted waveform, 610s: sound pressure level of initial waveform, 610p: sound pressure level of initial waveform, 610f: sound pressure level of initial waveform, 620s: sound pressure level of initial waveform, 620p: sound pressure level of initial waveform, 620f: sound pressure level of initial waveform, 630s: sound pressure level of initial waveform, 630p: sound pressure level of initial waveform, 630f: sound pressure level of initial waveform, 660s: sound pressure level of adjusted waveform, 660*p*: sound pressure level of adjusted waveform, 660*f*: sound pressure level of adjusted waveform, 670*s*: sound pressure level of adjusted waveform, 670*p*: sound pressure level of adjusted waveform, 670*f*: sound pressure level of adjusted waveform, 680*s*: sound pressure level of adjusted waveform, 680*p*: sound pressure level of adjusted waveform, 680*f*: sound pressure level of adjusted waveform, 710: band-stop filter, 810: table, 820: table, 830: table, 840: table, 850: table, 910: low-pass filter, 920*s*: gradient magnetic field waveform, 920*p*: gradient magnetic field waveform, 920*f*: gradient magnetic field waveform, 930: table

What is claimed is:

1. A magnetic resonance imaging device, comprising,
   an echo measurement section configured to irradiate a test subject placed in a static magnetic field, with a high-frequency magnetic field, along with applying a gradient magnetic field, according to an imaging condition and a pulse sequence designated by a user, and to receive echo signals generated from the test subject, and
   a database configured to store an adjusted gradient magnetic field waveform after adjustment of acoustic noise reduction in an initial waveform that is a gradient magnetic field waveform set in the pulse sequence, in association with the imaging condition and the pulse sequence designated by the user, wherein,
   the echo measurement section measures the echo signals by applying the adjusted gradient magnetic field waveform to the pulse sequence, and
   the adjusted gradient magnetic field waveform is obtained by an adjusted gradient magnetic field adjuster by filtering out a frequency band of the initial waveform to generate a filtered waveform, the frequency band having a pressure level equal to or higher than a predetermined level, and thereafter shaping the filtered waveform so that the imaging condition is satisfied.

2. The magnetic resonance imaging device according to claim 1, wherein,
   the gradient magnetic field waveform adjuster is configured to adjust the initial waveform, being the gradient magnetic field waveform set in the pulse sequence, and to obtain the adjusted gradient magnetic field waveform, wherein,
   the gradient magnetic field waveform adjuster comprises,
   a band-rejection section configured to filter out a specific band of the frequency band of the initial waveform, and to generate the filtered waveform, and
   a waveform shaper configured to perform the shaping of the filtered waveform so as to satisfy the imaging condition, and to obtain the adjusted gradient magnetic field waveform.

3. The magnetic resonance imaging device according to claim 2, wherein,
   the specific band to be filtered corresponds to a frequency band where a sound pressure level is equal to or higher than a predetermined level, in the frequency band of the initial waveform.

4. The magnetic resonance imaging device according to claim 3, wherein,
   the band-rejection section uses a response function inherent to the magnetic resonance imaging device, so as to calculate the sound pressure level of the initial waveform.

5. The magnetic resonance imaging device according to claim 4, further comprising,
   a response function calculator configured to apply a predetermined gradient magnetic field, so as to calculate the response function.

6. The magnetic resonance imaging device according to claim 5, comprising,
   a microphone disposed in proximity to the test subject, configured to collect sound that is generated therefrom, and
   a frequency analyzer configured to obtain a spectrum from the sound collected via the microphone, wherein,
   the response function calculator calculates the response function from the gradient magnetic field being applied and the spectrum.

7. The magnetic resonance imaging device according to claim 3, wherein,
   the gradient magnetic fields are applied to one or more different axis directions, respectively, and
   the band-rejection section filters out the frequency band of the gradient magnetic field that is applied to the axis direction having a summation of the sound pressure levels, the summation being equal to or higher than a predetermined level.

8. The magnetic resonance imaging device according to claim 2, wherein,
   the waveform shaper performs shaping of the filtered waveform during a high-frequency magnetic field irradiation period and the filtered waveform during an echo signal measurement period, in such a manner that the initial waveforms respectively during the periods are restored, so as to obtain the adjusted gradient magnetic field waveform.

9. The magnetic resonance imaging device according to claim 8, wherein,
   the gradient magnetic fields are applied to one or more different axis directions, respectively, and
   the waveform shaper further modifies the amplitude of the adjusted gradient magnetic field waveform in such a manner that a time integral value of the adjusted gradient magnetic field waveform, with respect to each axis for applying the gradient magnetic field, becomes equal to the time integral value of the initial waveform in the same axis direction.

10. The magnetic resonance imaging device according to claim 2, wherein,
    the waveform shaper modifies amplitude of the filtered waveform, so that average amplitude of the filtered waveforms during the high-frequency magnetic field irradiation period and average amplitude of the filtered waveform during the echo signal measurement period, become approximately equal to the average amplitude of the initial waveforms respectively during the periods, so as to obtain the adjusted gradient magnetic field waveform.

11. The magnetic resonance imaging device according to claim 10, wherein,
    the waveform shaper performs shaping of a waveform of the high-frequency magnetic field, in such a manner that variation of a slice profile caused by the adjusted gradient magnetic field waveform is reduced.

12. The magnetic resonance imaging device according to claim 11, further comprising,
    an image reconstructor configured to reconstruct an image from the echo signals, wherein,
    the image reconstructor performs gridding of the echo signals in accordance with the adjusted gradient magnetic field waveform during the time of receiving the echo signals, and thereafter, reconstructs an image.

13. The magnetic resonance imaging device according to claim 2, wherein,
  the gradient magnetic fields are applied to one or more different axis directions, respectively, and
  the band-rejection section filters out a frequency band which is different axis by axis to which the gradient magnetic fields are applied.

14. The magnetic resonance imaging device according to claim 2, wherein,
  the band-rejection section uses a band-stop filter for reducing a desired range of the frequency band, and filters out the specific frequency band.

15. The magnetic resonance imaging device according to claim 2, wherein,
  the frequency band that is filtered by the band-rejection section falls within the range from 0 to 3 kHz.

16. The magnetic resonance imaging device according to claim 2, wherein,
  the frequency band that is filtered by the band-rejection section is in the band around 2 kHz.

17. The magnetic resonance imaging device according to claim 2, wherein,
  a half value width of the frequency band that is filtered by the band-rejection section is a value nearly 2 kHz.

18. The magnetic resonance imaging device according to claim 2, wherein,
  the pulse sequence is a phase-compensation type GE sequence.

* * * * *